(12) United States Patent
Magoon et al.

(10) Patent No.: US 11,551,312 B1
(45) Date of Patent: Jan. 10, 2023

(54) MACHINE-LEARNING DRIVEN DATA ANALYSIS AND HEALTHCARE RECOMMENDATIONS

(71) Applicant: Nayya Health, Inc., New York, NY (US)

(72) Inventors: Akash Magoon, New York, NY (US); Aman Magoon, Fallston, MD (US); Mark Farnum, New York, NY (US); Daniel Young, New York, NY (US); Ishan Babbar, New York, NY (US); Satvik Gadamsetty, North Brunswick, NJ (US); Bradley Verdino, Long Island City, NY (US); David Feldman, New York (UA)

(73) Assignee: Nayya Health, Inc., New York, NY (US)

( * ) Notice: Subject to any disclaimer, the term of this patent is extended or adjusted under 35 U.S.C. 154(b) by 0 days.

(21) Appl. No.: 17/681,542

(22) Filed: Feb. 25, 2022

(51) Int. Cl.
*G06Q 40/08* (2012.01)
*G06F 16/2457* (2019.01)
*G16H 10/60* (2018.01)

(52) U.S. Cl.
CPC ......... *G06Q 40/08* (2013.01); *G06F 16/2457* (2019.01); *G16H 10/60* (2018.01)

(58) Field of Classification Search
CPC ..... G06Q 40/08; G16H 10/60; G06F 16/2457
See application file for complete search history.

(56) References Cited

U.S. PATENT DOCUMENTS

| | | |
|---|---|---|
| 9,690,538 B1* | 6/2017 | Doyle, III et al. |
| 2018/0150599 A1* | 5/2018 | Valdes et al. |
| 2020/0090791 A1* | 3/2020 | Lucena et al. |
| 2021/0257093 A1* | 8/2021 | Griffen et al. |

\* cited by examiner

*Primary Examiner* — Michael Tomaszewski
*Assistant Examiner* — William T. Monticello
(74) *Attorney, Agent, or Firm* — NovoTechIP International PLLC

(57) ABSTRACT

A data processing system for machine-learning driven data analysis implements obtaining digital healthcare service provider information associated with one or more digital healthcare service providers and query parameters information from a user searching for digital healthcare service providers that may provide digital healthcare services to employees of the user. The system analyzes query parameter information using a first machine learning model to obtain category information. The system analyzes the category information and the digital health service provider information to predict digital healthcare service providers that provide services that the user may be interested in provided to the employees. These predictions are provided to the user as digital healthcare service recommendations.

20 Claims, 16 Drawing Sheets

Digital Health Service Provider Portal – Getting Started

We will guide you through a series of questions to collect information about your company and the services you provide. This information will help us to match you with users who may benefit from these services.

Background Information:

Enter a description of the services your company offers:

Select a logo for your company that may be presented to users:

Select the type of services that your company offers. You may select more than one. We will follow up with additional information questions to collect more information regarding these services so that we can better match you with users who in need of such services. You may return to this screen at any time to select or deselect services

Services Offered:
☐ Mental Health and Counseling
☐ Drug Counseling and Rehabilitation
☐ Nutrition and Weight Loss
☐ Physical Therapy
☐ Prenatal, Pregnacy, and Post-Natal Assistance and Counseling
☐ Sleep Health
☐ Other (we will walk you through setting up other types of services you office)

Cancel   Next

FIG. 5

Employer Dashboard – Add Digital Health Service Providers

We will guide you through a series of questions to determine the types of services that you may wish to offer your employees. We will present you with providers who offer these types of services and pricing information for various service plans offered by these providers. We will also guide you through setting up a new service plan with one or more selected providers and can also connect you with a customer service representative from the service provider to help answer any questions you may have regarding the services offfered.

Types of Services to be Explored:
☐ Mental Health and Counseling
☐ Drug Counseling and Rehabilitation
☐ Nutrition and Weight Loss
☐ Physical Therapy
☐ Prenatal, Pregnancy, and Post-Natal Assistance and Counseling
☐ Sleep Health
☐ Other (we will walk you through setting up other types of services you office)

Next

Cancel

Employer Dashboard – Add Providers – Provider Details

You are currently exploring the offerings by service providers under the Mental Health and Counseling category of services. You can return to the Employer Dashboard at any time by selecting Return to Dashboard or browse through the available providers by selecting Next Provider or Previous Provider. You may also select the Bookmark Provider to save a provider to your list of providers under My Providers on the Employer Dashboard.

CounselSpace ( Bookmark Provider )

CounselSpace offers counseling via text, audio, or video at no cost to you. To explore the service plans offered by CounselSpace, click on "Let's Explore the Service Plans" below and we'll connect you with CounselSpace to guide you through setting up a counseling session.

( Let's Explore the Service Plans )

If you have any questions regarding the counseling services provided by CounselSpace or the service plans available to your company, please click "Chat Now" to connect with a CounselSpace representative who can assist you.

( Chat with Representative )

( < Back to Dashboard )    ( Next Category > )    ( Next Provider > )

Employer Portal – Dashboard – My Providers

The following are a list of service providers that you bookmarked. You can select a provider to find out more information about the services plans offered by a provider and the service plan to which are currently subscribed for that provider (if any).

CounselSpace ( Get Provider and Plan Information )

Current subscription: Medium-sized Entity Full Counseling Benefits Plan. Select Get Provider and Plan Information to get details of your current subscription.

MaterniHealth ( Get Provider and Plan Information )

Current subscription: Full Coverage without Copay for 100-250 employees. Select Get Provider and Plan Information to get details of your current subscription.

DialyServ of New York ( Get Provider and Plan Information )

Current subscription: NONE. Select Get Provider and Plan Information to explore the service plans offered by DialyServ of New York.

( < Back to Dashboard )          ( Next > )

Employee Benefits Dashboard – Benefit Recommendation

Anna
Your employer provides free counseling services through CounselSpace. You could save up to $175 per session based on the cost of your recent psychiatrist visit.

CounselSpace

Offers counseling via text, audio, or video at no cost to you. If you would like to get started with your online counseling benefits with CounselSpace, click on "Let's get started" below and we'll connect you with CounselSpace to guide you through setting up a counseling session.

( Let's Get Started! )

If you have any questions regarding the counseling services provided by CounselSpace, please click "Chat Now" to connect with a CounselSpace representative who can assist you.

( Chat with Representative )

( < Back to Dashboard )

MACHINE-LEARNING DRIVEN DATA ANALYSIS AND HEALTHCARE RECOMMENDATIONS

BACKGROUND

Digital healthcare point solutions are healthcare providers that offer virtual clinics that compete with traditional healthcare providers. The digital healthcare point solutions that often deliver high-quality care at a fraction of the cost of traditional healthcare providers and at a dramatically higher scale. In the past, employers worked with large insurance companies to manage the health insurance and provide a network of doctors for their employees. However, employers have recognized that digital healthcare point solutions can supplement the benefit provided to their employees and may realize significant cost savings for both the employers and the employees.

Many employees underutilize their insurance and benefits because they are unaware of and/or forget to use all the coverage provided thereby. The introduction of digital healthcare point solutions further complicates matters. Consequently, valuable benefits may go unused by the employees. Hence, there is a need for improved systems and methods that provide a technical solution for solving the technical problem of automatically analyzing the benefits available to a user and providing recommendations to assist the user in utilizing the available benefits.

SUMMARY

An example data processing system according to the disclosure may include a processor and a computer-readable medium storing executable instructions. The instructions when executed cause the processor to perform operations including obtaining digital healthcare service provider information associated with one or more digital healthcare service providers to provide digital healthcare point solutions to employees of an employer; converting the digital healthcare service provider information from a first format to a second format to generate standardized digital healthcare service provider information, the second format being associated with a standard schema; receiving, from the client device associated with a user, query parameters information identifying characteristics of digital healthcare service providers for providing digital care health services; converting the query parameters information from a third format to a fourth format to generate standardized query parameter information, the fourth format being associated with the standard schema; providing the standardized query parameter information as an input to a first machine learning model; analyzing the standardized query parameter information to obtain category information, the first machine learning model being trained using first training data formatted according to the standard schema to recognize a category or categories of services associated with the standardized query parameter information; providing the category information and the digital healthcare service provider information as an input to a second machine learning model; analyzing the category information and the digital healthcare service provider information using the second machine learning model to obtain digital healthcare service recommendations, the second machine learning model being trained using second training data formatted according to the standard schema to predict digital health services that the employer may provide to the employees of the employer based on the category information and categories of digital health services included in the digital healthcare service provider information; and providing, via a network connection, the digital healthcare service recommendations to the computing device associated with the user.

An example method implemented in a data processing system for machine-learning driven data analysis and reminders includes obtaining digital healthcare service provider information associated with one or more digital healthcare service providers to provide digital healthcare point solutions to employees of an employer; converting the digital healthcare service provider information from a first format to a second format to generate standardized digital healthcare service provider information, the second format being associated with a standard schema; receiving, from the client device associated with a user, query parameters information identifying characteristics of digital healthcare service providers for providing digital care health services; converting the query parameters information from a third format to a fourth format to generate standardized query parameter information, the fourth format being associated with the standard schema; providing the standardized query parameter information as an input to a first machine learning model; analyzing the standardized query parameter information to obtain category information, the first machine learning model being trained using first training data formatted according to the standard schema to recognize a category or categories of services associated with the standardized query parameter information; providing the category information and the digital healthcare service provider information as an input to a second machine learning model; analyzing the category information and the digital healthcare service provider information using the second machine learning model to obtain digital healthcare service recommendations, the second machine learning model being trained using second training data formatted according to the standard schema to predict digital health services that the employer may provide to the employees of the employer based on the category information and categories of digital health services included in the digital healthcare service provider information; and providing, via a network connection, the digital healthcare service recommendations to the computing device associated with the user.

An example machine-readable storage medium according to the disclosure on which are stored instructions which when executed cause a processor of a programmable device to perform operations of obtaining digital healthcare service provider information associated with one or more digital healthcare service providers to provide digital healthcare point solutions to employees of an employer; converting the digital healthcare service provider information from a first format to a second format to generate standardized digital healthcare service provider information, the second format being associated with a standard schema; receiving, from the client device associated with a user, query parameters information identifying characteristics of digital healthcare service providers for providing digital care health services; converting the query parameters information from a third format to a fourth format to generate standardized query parameter information, the fourth format being associated with the standard schema; providing the standardized query parameter information as an input to a first machine learning model; analyzing the standardized query parameter information to obtain category information, the first machine learning model being trained using first training data formatted according to the standard schema to recognize a category or categories of services associated with the standardized query parameter information; providing the category information and the digital healthcare service provider information as an input to a second machine learning model; analyzing the category information and the digital healthcare service provider information using the second machine learning model to obtain digital healthcare service recommendations, the second machine learning model being trained using second training data formatted according to the standard schema to predict digital health services that the employer may provide to the employees of the employer based on the category information and categories of digital health services included in the digital healthcare service provider information; and providing, via a network connection, the digital healthcare service recommendations to the computing device associated with the user.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

The drawing figures depict one or more implementations in accord with the present teachings, by way of example only, not by way of limitation. In the figures, like reference numerals refer to the same or similar elements. Furthermore, it should be understood that the drawings are not necessarily to scale.

FIG. 5 shows an example user interface for a provider portal that may be implemented by the CAAS.

FIGS. 6A, 6B, and 6C show examples of user interfaces for an employer portal that may be implemented by the CAAS.

FIGS. 7A and 7B show examples of user interfaces for an employee portal that may be implemented by the CAAS.

DETAILED DESCRIPTION

Figure 1:
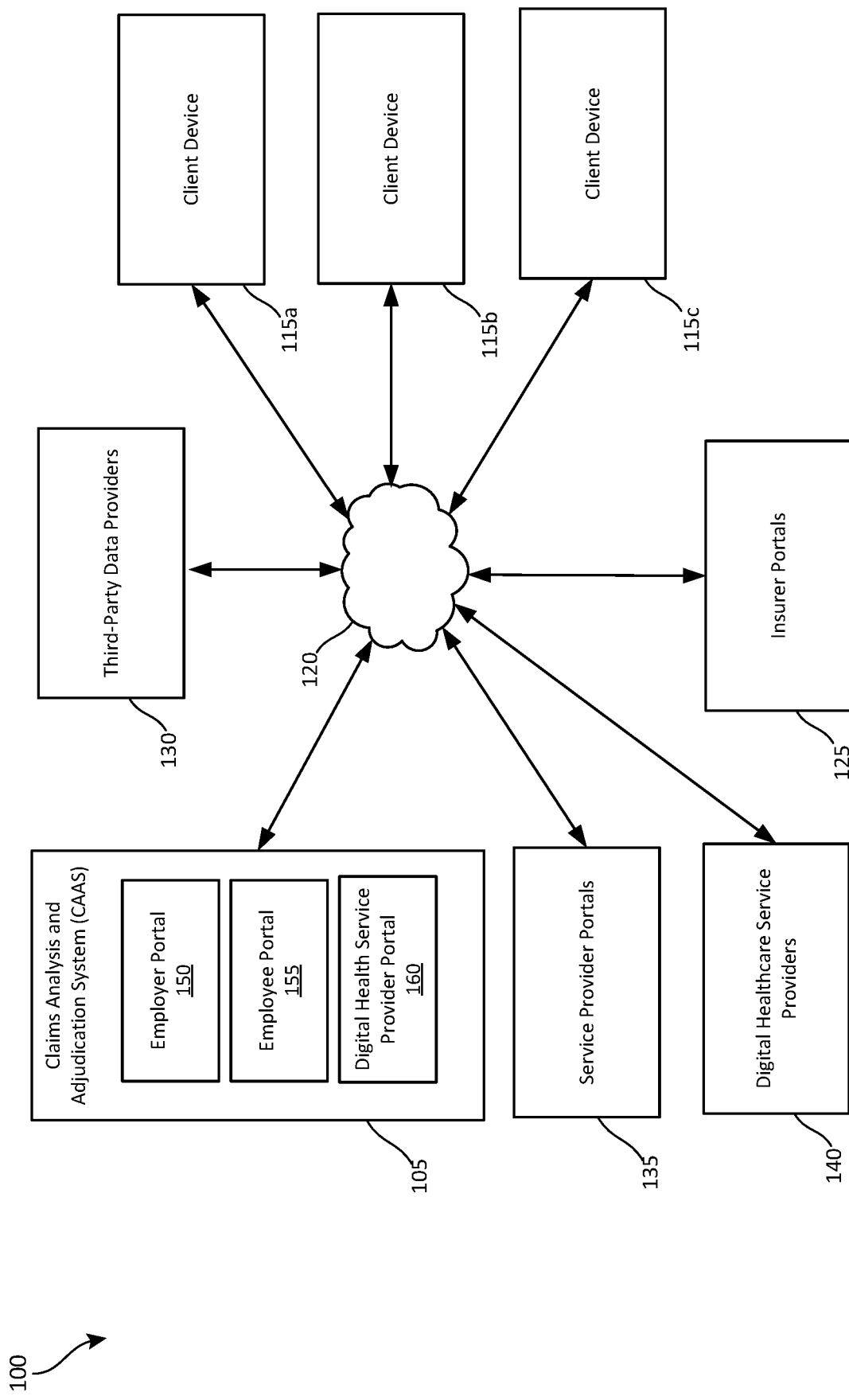
FIG. 1 is a diagram showing an example computing environment in which the techniques disclosed herein may be implemented.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

Techniques are described herein for machine-learning driven recommendations and reminders to a user for optimizing the usage of the benefits provided by the user's employer. The employer may offer an insurance plan that includes a bundle of insurance polices in addition to one or more digital healthcare point solutions. The digital healthcare point solutions may supplement the coverage provided by the insurance policies. The digital healthcare point solutions may provide various benefits to the user that may be no cost or low-cost to the user. These services may provide the user with significant healthcare cost savings compared with similar solutions offered by traditional healthcare services providers covered under the insurance plan. The techniques provided herein provide a technical solution for identifying benefits that the user may have left unutilized or underutilized by analyzing policy information, insurance consumption information, and user demographic information to provide recommendations for the user for utilizing various benefits associated with their insurance plan. A technical benefit of this approach is that the machine learning models may recognize patterns in the insurance claims and/or the demographic information of the user to recommend benefits offered by the digital healthcare point solutions that may not otherwise be evident to a user and/or may be overlooked by the user. These techniques may not only identify benefits that the user may utilize to maintain their health and well-being but also provide recommendations where the user may save significantly on medical spending. Another technical benefit provided by the techniques described herein is that the machine learning models may be trained using data that has been parsed and standardized into a standard schema. Furthermore, the data to be analyzed by the machine learning models may also be parsed and standardized. As a result, the machine learning models are receiving data in a format that utilizes descriptions that are consistent with the training data used to train the models. Consequently, the predictions provided by the models may be significantly improved in comparison to models which are not trained using such a technique. The techniques provided herein also provide for substantially real-time analysis of information from a combination of data sources that may also significantly improve the predictions provided by the machine learning models and provide the user with recommendations that are more likely to provide for the user's needs. These and other technical benefits of the techniques disclosed herein will be evident from the discussion of the example implementations that follow. Furthermore, the techniques provided herein satisfy a long-felt need for improving the utilization of benefits available to users. Due to the complexity of the various policies and the rapidly evolution of digital healthcare point providers available to the user, the user may often overlook or fail to completely utilize the benefits available to them. The solution provided herein provides substantially real-time analysis of the user's benefits, the user's utilization of these benefits, and other user-related data to provide recommendations to the user for optimizing their available benefits.

FIG. 1 is a diagram showing an example computing environment 100 in which the techniques disclosed herein for insurance claims analysis and adjudication may be implemented. The computing environment 100 may include a claims analysis and adjudication system (CAAS) 105, one or more client devices 115, one or more insurer portals 125, one or more provider portals 135, one or more third-party data providers 130, and digital healthcare service providers 140. The CAAS 105 may also provide an employer portal 150, an employee portal 155, and a third-party health-provider portal 160. The example implementations shown in FIG. 1 include three client devices 115a, 115b, and 115c, but the techniques described herein may be used with a different number of client devices 115. The client devices 115a, 115b, and 115c may communicate with the CAAS 105, the insurer portals 125, service provider portals 135, and/or the third-party data providers via the network 120. The CAAS 105 may also communicate with the client devices 115a, 115b, and 115c, the insurer portals 125, the service provider portals 135, and/or the third-party data providers 130 via the network 120. The network 120 may include one or more wired and/or wireless public networks, private networks, or a combination thereof. The network 120 may be implemented at least in part by the Internet.

The client devices 115a, 115b, and 115c may be used by an insured to access the services provided by the CAAS 105, insurance information from the insurer portals 125, and/or information from the third-party data providers 130. The client devices 115a, 115b, and 115c are each a computing device that may be implemented as a portable electronic device, such as a mobile phone, a tablet computer, a laptop computer, a portable digital assistant device, a portable game console, and/or other such devices. The client devices 115a, 115b, and 115c may also be implemented in computing devices having other form factors, such as a desktop computer, vehicle onboard computing system, a kiosk, a point-of-sale system, a video game console, and/or other types of computing devices. While the example implementation illustrated in FIG. 1 includes three client devices, other implementations may include a different number of client devices. The client devices 115a, 115b, and 115c may be used to access the applications and/or services provided by the insurer portals 125 and/or the CAAS 105.

The insurer portals 125 may be supplied by insurance providers as a means for insured users to access their policy information, make policy payments, obtain new policies, to submit claims on existing policies, and/or perform other actions related to the managing the insured's insurance. An insured user may have policies with multiple insurers, and thus, may have to access multiple insurer portals 125 to obtain information related to each of their insurance policies. Consequently, the insured user must learn to navigate multiple insurance portals that may have significantly different layouts in order to access their policy information, submit claims and/or check on claim status, or perform other actions related to their policy.

The service provider portals 135 may provide a means for doctors, dentists, optometrists, and/or other medical professionals to submit claims to the insurers on behalf of an insured user. The service provider portals 135 may provide means for the providers to check on the status of a claim with an insurer. The service provider portals 135 may also permit the providers to amend and/or resubmit claims.

The digital healthcare service providers 140 provide digital healthcare point solutions. The digital heath service providers 140 may contract with employers to provide their services to employees of the employers. The digital healthcare service providers 140 may also provide these services to individual users requiring such services. The digital healthcare service providers 140 may provide a virtual clinic that users may access from a smart phone, tablet, computer, or other such client device 115. The digital healthcare service providers 140 may provide various types of telemedicine services, counseling, and guidance to users. This approach enables the digital healthcare service providers 140 to provide high quality care to users regardless of the geographical location of the providers and the users. Consequently, the digital healthcare service providers 140 may provide such services at a significantly lower cost than traditional healthcare providers, which bear the significant cost of brick-and-mortar physical locations for their offices and/or clinics.

The CAAS 105 provides a cloud-based or network-based portal for accessing the services provided by the CAAS 105. The CAAS 105 may be configured to provide secure and delegated access to insurance claims for insured users. The CAAS 105 may implement a claims application programming interface (API) infrastructure that allows the insured users to access their insurance claims data and to provide various services such as claims analysis and adjudication services, guidance for optimizing prescription benefits, guidance for optimizing medical spending account (MSA) usage, guidance for proactive benefits engagement, services which may assist the insured in selecting a bundle of insurance products that satisfies the insured requirements, and/or other services related to optimizing the insurance coverage and utilization by the insured. Among the services provided by the CAAS 105, the CAAS 105 provides substantially real-time claims analysis and adjudication. The CAAS 105 may utilize a machine-learning model or models trained to analyze the claims to guide the user through submitting the claims to the appropriate insurer and to provide other advice for optimizing the use of the coverage provided to the user by their policies. The CAAS 105 may also respond to changes in the demographic data of the user and may provide a proposed bundle of insurance policies that meet the changing needs of the user. The example implementations which follow provide additional details describing these and other features of the CAAS 105.

The CAAS 105 may be configured to collect policy and claims information for users from the insurer portals 125, to analyze the information included in the policy information to obtain coverage information. The coverage information may include which types of claims are covered by each policy, the limits of coverage provided by each policy, other information that may be used to determine whether an insurer may cover a particular claim, or a combination thereof. The CAAS 105 may be configured to implement a set of secure and authenticated pipelines that are configured to allow members to link to their accounts with their insurance providers to obtain plan information, claims information, or both. The CAAS 105 may provide a user interface that provides a list of supported insurers. The user may select an insurer from the list of supported insurers and the user interface guides the user through setting up the connection with the user's account with that insurer. The user may securely provide authentication details that permit the CAAS 105 to securely access the policy information and/or claims information provided through the insurer portals 125. The CAAS 105 may access the policy information, claims information, or both, analyze this information, and convert the information to a unified and standardized schema for this information. The standardized information may be stored by the CAAS 105 to provide various services to user, which will be discussed in greater detail with respect to the example implementation of the CAAS 105 shown in FIGS. 2 and 3.

The CAAS 105 may also implement an employer portal 150. The employer portal 150 may provide a dashboard user interface that enables employers to access information associated with the insurance plans and benefits provided to their employees. These benefits may include insurance policy information as well as information about service providers with which the employer may have contracted to provide services to the employee. These services may include services provided by one or more digital healthcare service providers. The employer portal 150 may include means for viewing, accessing, or modifying the services that the employer has obtained on behalf of their employees. The employer may cover all or part of the cost associated with the services provided by the digital healthcare service providers. The employer dashboard may also permit the employer to search for insurers and/or digital healthcare service providers and obtain insurance plan information and/or service plan information from the insurers and/or digital healthcare service providers. The dashboard may also guide the employer through setting up new insurance coverage and/or a new service plan with an insurer and/or a digital health service provider. Additional details of the employer portal 150 are described in the examples which follow.

The CAAS 105 may implement an employee portal 155. The employee portal 155 may provide a dashboard user interface that enables employees to access information associated with the benefits provided by their employer, information about insurance claims and prescriptions for the user and/or others covered by the user's insurance, information on benefits utilization and how the user may save money by adjusting how they utilize their benefits. These recommendations may include recommendations, also referred to herein as "nudges," that suggest that the user may utilize services provided by one or more digital health services of the digital healthcare service providers 140. These recommendations may identify unused or underutilized benefits that include those provided by digital healthcare service providers 140. The recommendations may also include estimated cost savings that the user may experience by utilizing the digital healthcare service providers 140 instead of the services of one or more conventional services providers whose services may be significantly more expensive and may not be covered by the user's insurance.

The CAAS 105 may implement a digital health service provider portal 160. The digital health service provider portal 160 may implement a dashboard user interface that enables digital healthcare service providers to provide information to advertise the services that they provide. Employers may search this information to identify digital healthcare service providers that offer services that they wish to offer to their employees. The CAAS 105 may also use the information obtain from the digital healthcare service providers to match the services with the predicted needs of employees whose employers have contracted with the digital healthcare service providers. Additional details of how the CAAS 105 may match the predicted needs of the employees with the services offered by the digital healthcare service providers 140 are discussed in detail in the examples which follow.

The third-party data providers 130 are additional data sources that may be accessed by the CAAS 105 to obtain additional information for a user. The CAAS 105 may be configured to use the third-party data to supplement information collected from the user. The CAAS 105 may be configured to collect at least some demographic information from the user by presenting a set of dynamically generated questions to the user. The questions presented to the user may be dynamically selected based at least in part on the user's responses to previous questions, to information included in the third-party data, or a combination thereof. The third-party information and/or information that may be collected from the user may include, but is not limited to, the user's medical history, past insurance consumption, the user's financial profile (debts, assets, liabilities), credit history, family information, psychographics, interests, occupation, salary, physical activity, and other information that may be used by the CAAS 105 to facilitate providing insurance plan recommendations to the user. The CAAS 105 may query the third-party data providers 130 for information and may reformat the data into a standard schema used by the CAAS 105 for storing and analyzing the data. The CAAS 105 may also be configured to disambiguate the data received from the third-party data sources where the data includes information associated with multiple people who may or may not be the user. Additional details of data disambiguation are provided in the examples which follow.

Figure 2:
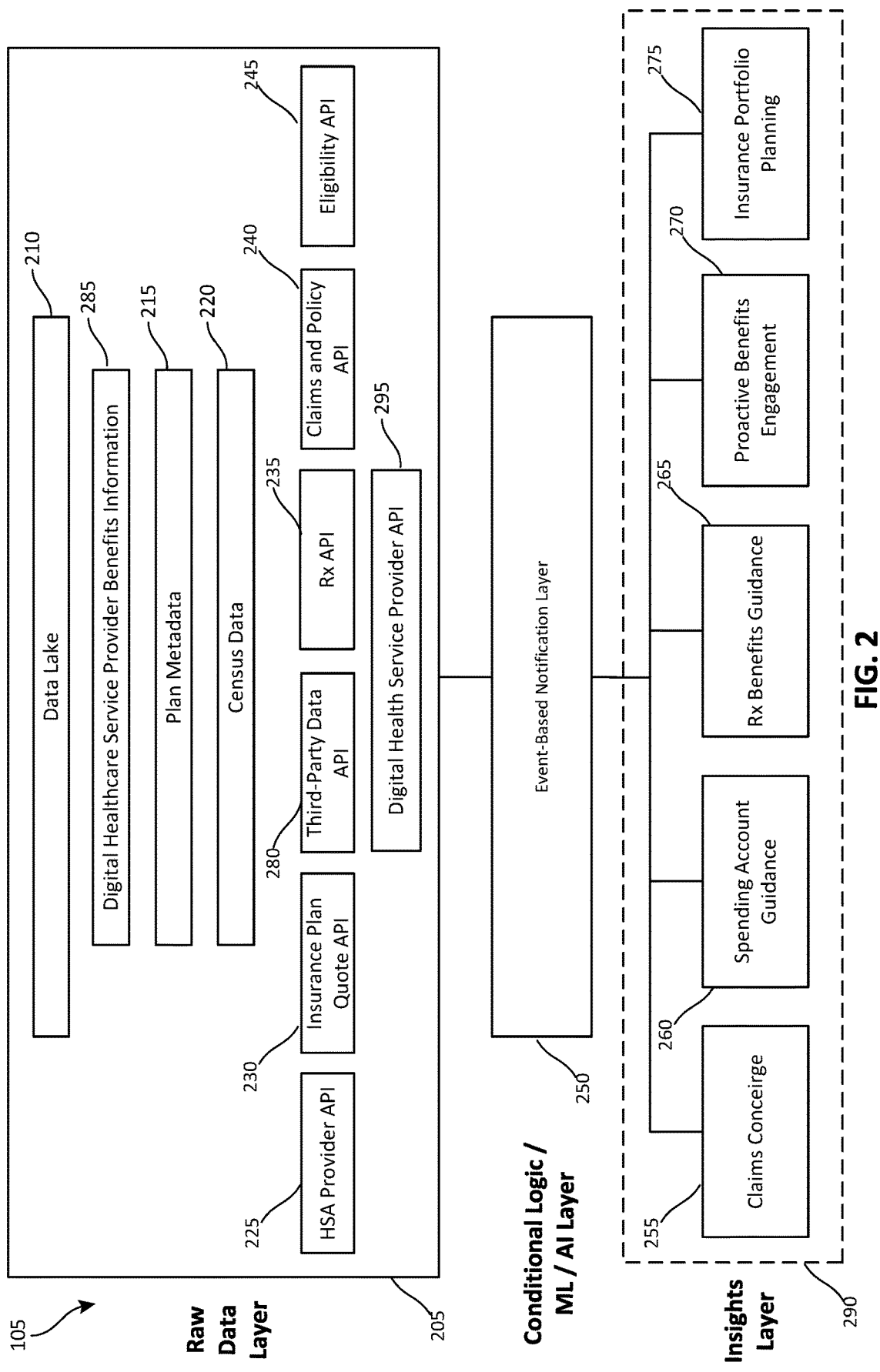
FIG. 2 is a diagram of an example architecture that may be used, at least in part, to implement the claims analysis and adjudication system (CAAS) shown in FIG. 1.

FIG. 2 is a diagram of an example implementation of a CAAS 105 shown in FIG. 1 that shows additional elements of the CAAS 105. The CAAS 105 shown in FIG. 2 includes three layers: (1) a raw data layer 205, (2) an event-based notification layer 250, and (3) an insights layer 290. The raw data layer 205 may be configured to obtain insurance data for users from various data sources, to convert this data to a unified and standardized schema, and to store the user data for analysis by the event-based notification layer 250 and/or the insights layer 290 to provide various insurance-related services to the users. The raw data layer 205 may also be configured to obtain digital healthcare service provider information from the digital healthcare service providers 140, to convert this data to the unified and standard schema, and to store the digital healthcare service provider information for analysis by the event-based notification layer notification layer 250 and/or the insights layer 290 to provide recommendations to employers and/or users regarding the services provided by the digital health services providers 140. Additional details of the functions of each of these layers will be described in greater detail in the examples which follow. In some implementations, the functions of each of these layers may be grouped together into a different number of functional layers. Furthermore, the functionality of each of the layers may be implemented on separate servers in some implementations, and the servers may be communicably coupled over public and/or private network connections to permit the various components of the CAAS 105 to exchange and analyze data.

The raw data layer 205 may include a data lake 210, a plan metadata data store 215, a census data datastore 220, a health savings account (HSA) provider API 225, an insurance plan quote API 230, a prescription API 235, a claims and policy API 240, an eligibility API 245, and a third-party data API 280. The APIs provide pipelines for obtaining data that that the CAAS 105 may use to provide various insurance-related services. User data may be protected by secure and authenticated pipelines when accessing sensitive data. The CAAS 105 may guide a user through setting up authentication with the external data sources to allow the CAAS 105 to securely access the user data.

Figure 3:
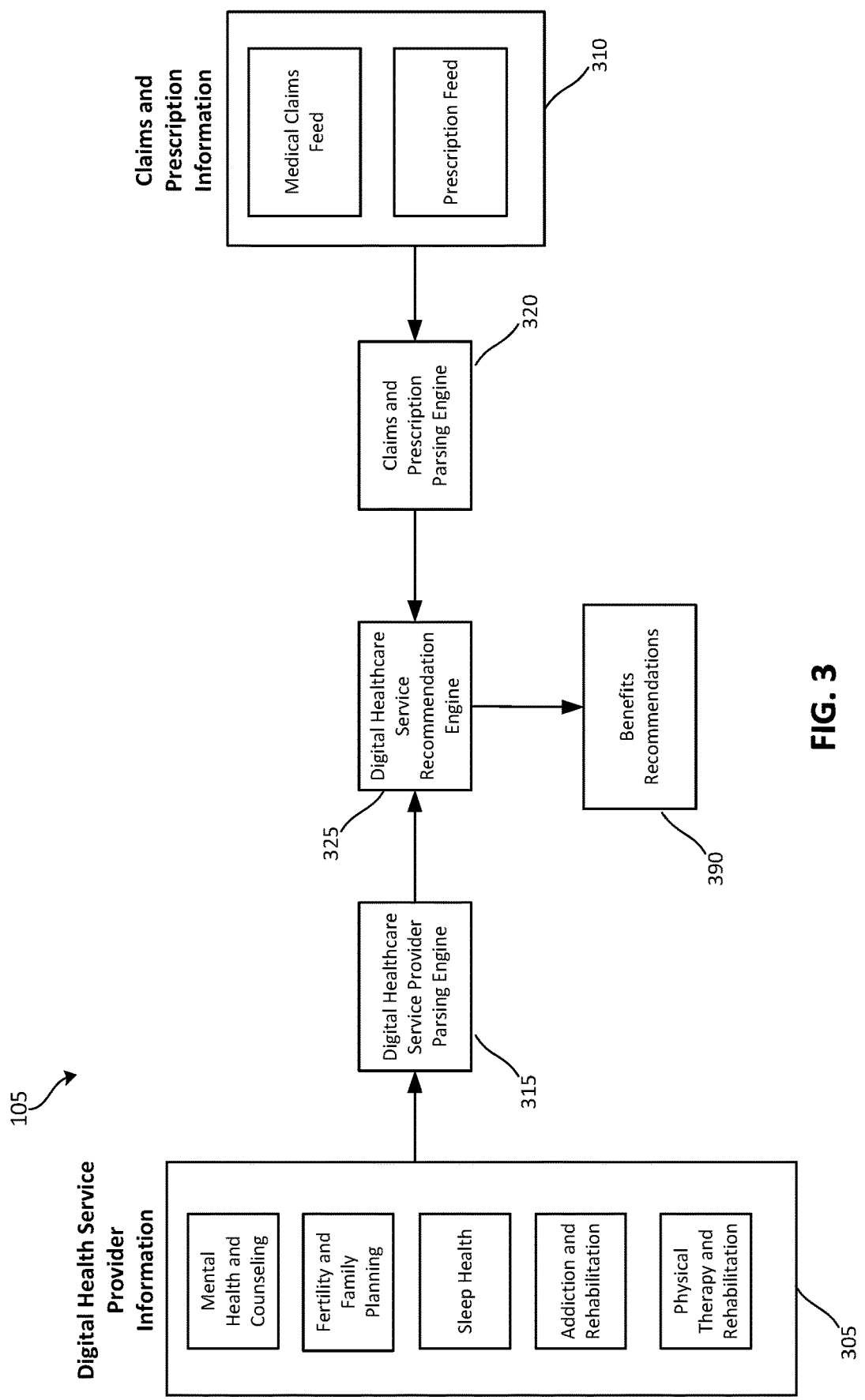
FIG. 3 is a diagram of an example architecture that shows additional details of a CAAS which may be used to implement the CAAS shown in FIGS. 1 and 2.

The data lake 210 may be used to store raw user data, raw claims data, raw policy data, and raw digital healthcare service provider information that has been obtained from one or more external data sources, such as but not limited to the insurer portals 125, the third-party data providers 130, and the digital healthcare service providers 140. Raw data, as used herein, refers to an original data format in which the data was obtained from the external data source. The format of the raw data may depend on the type of data and the external data source from which the data was obtained. The raw data may be retained in the data lake 210, and the raw data 210 may be processed into a standard schema by one or more parsing engines of the CAAS 105. The standard schema defines a set of logical data structures that may be used by the CAAS 105 storing and analyzing data. FIG. 3, which will be discussed in greater detail below, includes two parsing engines, a digital healthcare service provider parsing engine 315 and a claims and prescription parsing engine 320. While the example shown in FIG. 3 includes two separate parsing engines, the functionality of the parsing engines may be combined into a single parsing engine or into a different number of parsing engines than those shown in FIG. 3. Furthermore, additional parsing engines or parsing engine functionality may be provided, such as but not limited to a policy parsing engine for parsing policy information obtained from one or more insurance providers and HSA information parsing engine for parsing information obtained from one or more HSA providers. The standardized data may be stored in the plan metadata 215 and/or the digital health service provider benefits information 285.

The policy data may include coverage information, including but not limited to the types of claims are covered by each policy, the limits of coverage provided by each policy, other information that may be used to determine whether an insurer may cover a particular claim for a user. The census data 220 may include demographic information that is collected from the user by the CAAS 105, information about the user obtained from third-party data providers 130, information obtained from the insurer portals 125, and/or other information about the users that may be used by the CAAS 105 to provide recommendations to the user regarding insurance-related issues. The user-related data obtained from these various sources may be formatted into a standard schema by one or more parsing engines of the CAAS 105 and stored in the census data 220.

The raw data layer 205 shown in FIG. 2 includes six API units configured to implemented APIs for accessing data from various sources. Some implementations of the raw data layer 205 of the CAAS 105 may include a different number of APIs for accessing data from the various data sources. The types of data sources accessed and processed by the raw data layer may depend at least in part on the functionality provided by the insights layer 290 discussed in greater detail in the examples which follow.

The digital health service provider API 295 is configured to obtain service information from the digital healthcare service providers 140. The CAAS 105 may provide a digital health service provider portal 160 that may provide a user interface for digital healthcare service providers to access the functionality of the CAAS 105 and to advertise their services to employers and employees. The digital health service provider API 295 may be used to exchange information between the CAAS 105 and the servers of the digital healthcare service providers 140. For example, the digital health service provider 140 may obtain information for covered employees from the CAAS 105 via the digital health service provider API 295.

The claims and policy API 240 is configured to obtain policy information and/or insurance claims information from insurers via the insurer portals 125. As discussed in the preceding examples, the CAAS 105 may be configured to provider a user interface that guides the user through linking their account with the CAAS 105 to their accounts with their insurers. The claims and policy API 240 may be configured to retrieve policy information and/or claims information from each insurer and store the raw data in the data lake 210. The insurance policy information may be converted to the standard schema by the digital healthcare service provider parsing engine 315 and the claims information may be converted to a standard schema by the claims and prescriptions parsing engine 320 shown in FIG. 3.

The policy information for users may be kept up to date in substantially real-time. The claims and policy API 240 may be configured to periodically check for updates to the policy information for users. The claims and policy API 240 may also check for updates to the policy information for the user in response to a request from the event-based notification layer 250 or the insights layer 290. In some implementations, the claims and policy API 240 may receive updates to the claims information and/or the policy information from the insurer in response to the changes or renewal of a policy or in response to claims being submitted to the insurer for reimbursement.

The HSA provider API 225 may be configured to obtain information from one or more HSA providers. The HSA provider API 225 can obtain information associated with the HSA account of a user, such as but not limited to the current balance, historical reimbursement information for claims reimbursed by the HSA account, and/or other information associated with the usage of the HSA account. The HSA information may be used by the CAAS 105 to build a historical model of the number and types of claims submitted for reimbursement by the user and to make predictions for recommended future funding of the HSA based on the historical usage. The HSA information may be obtained by the HSA provider API 225 may be stored in data lake 210. The HSA information may be converted to the standard schema by an HSA parsing engine (not shown) implemented by the raw data layer 205. The HSA account information may also be considered by the CAAS 105 when analyzing the insurance coverage of the user and for recommending coverage that accommodates the needs of the user. While the examples discussed herein discuss the use of HSAs, the HSA provider API 225 may also be configured to obtain information for flexible spending accounts (FSAs) as well. FSAs are another type of spending account that are typically associated with an employer. FSAs may have different eligibility criteria for enrollment and different contribution limits than HSAs. Furthermore, unused funds in an FSA may be forfeited at the end of the calendar year while unused funds in an HSA typically may roll over to the next year.

The prescription API 235 may be configured to obtain prescription price information from a pharmacy benefits manager (PBM). Information regarding the prescriptions that a user has been prescribed may be obtained directly from the user and/or determined based on the claims information obtained from the insurance providers via the claims and policy API 240. The prescription price information may be utilized by the prescription benefits guidance unit 265 to provide recommendation for saving money on prescriptions.

The insurance plan quote API 230 may be configured to obtain quotes for insurance coverage from insurers that may be used by the CAAS 105 to create a comprehensive bundle of insurance policies for a user based at least in part on predicted insurance consumption by the user. The insurance plan quote API 230 may be configured to submit requests for quotes to insurers for medical insurance, dental insurance, accident insurance, hospital indemnity insurance, auto insurance, and/or other types of insurance. The insurance portfolio planning unit 275 may use the quote information to build a comprehensive insurance plan for the user that is based on the needs of the user. The insurance portfolio planning unit 275 may determine the needs of the user based on user data that includes, but is not limited to, the user's medical history, past insurance consumption, the user's financial profile (debts, assets, liabilities), family information, psychographics, interests, occupation, salary, physical activity, and/or other information that may be used to infer the needs of the user.

The eligibility API 245 may be configured to verify enrollment of a user with an insurer. The API 245 may be used to determine whether the user is covered by a particular policy and whether the user is eligible for certain types of claims to be reimbursed by the insurer. The eligibility information may be utilized by the CAAS 105 to determine whether a particular claim or type of claims may be covered by a particular insurer. The eligibility information may be accessed substantially in real-time so that recommendations provided by the CAAS 105 are based on current enrollment status of the user.

The third-party data API 280 may be configured to submit queries for third-party data to the third-party data provider 130. The third-party data sources may include but are not limited to sources of medical history data, financial profile information, credit history information, marital status information and/or family information, occupation, salary, and/or other information that may be used by the CAAS 105 to provide various recommendations to the user. The third-party data API 280 may be used by the various components of the CAAS 105 to query the various data sources for third party data.

The event-based notification layer 250 may utilize conditional logic, machine learning models, and/or artificial intelligence systems for analyzing the data obtained and/or generated by the raw data layer 205. The event-based notification layer 250 may be configured to analyze the data from the raw data layer 205 to support the functionality of the services provided by the insights layer 290. The event-based notification layer 250 may utilize one or more machine learning models to analyze the data maintained by the raw data layer 205. The event-based notification layer 250 may implement elements of the digital healthcare service recommendation engine 325 shown in FIGS. 3 and 4.

The insights layer 290 may provide various services to the user based on the analysis of the data by the event-based notification layer 250. The insights layer 290 includes a claims concierge unit 255, a spending account guidance unit 260, a prescription benefits guidance unit 265, a proactive benefits engagement unit 270, and an insurance portfolio planning unit 275.

The claims concierge unit 255 may be configured to analyze claims data and to provide recommendations to the user for submitting the claims to an insurer. The claims concierge unit 255 may be configured to automatically analyze claims data to identify claims that may be paid by an insurer. The claims concierge unit 255 may also provide recommendations in response to a request from a user to analyze one or more pending insurance claims.

The spending account guidance unit 260 may provide guidance to the user for optimizing the funding of the MSA based on prior health plan consumption and utilizing the MSA funds to reimburse medical claims costs. The prescription benefits guidance unit 265 may provide guidance to the user for providing prescription price guidance to the user including prices at which prescriptions medications are being offered at pharmacies located near the user.

The proactive benefits engagement unit 270 may provide recommendations to the user for optimizing the usage of their benefits. The proactive benefits engagement unit 270 may be configured to provide meaningful and actionable notifications to encourage users to engage with the benefits provided by their insurance policies. The proactive benefits engagement unit 270 may consider the personal finances of the user and other factors when making recommendations to the user regarding the usage of the user's benefits. The proactive benefits engagement unit 270 may provide recommendations regarding digital health service provider benefits available to the user. Additional features of the proactive benefits engagement unit 270 are provided in the examples which follow.

The insurance portfolio planning unit 275 may provide recommendations to the user for building insurance bundles that consider the user's demographics, risk aversion of the user, and the needs of the user.

FIG. 3 is a diagram that shows an example implementation of a digital healthcare service recommendation engine 325 that may be implemented by the CAAS 105. The digital healthcare service recommendation engine 325 may be configured to provide machine-learning driven recommendations for assisting the user in utilizing their benefits provided by one or more digital healthcare service providers. Additional details of the services provided by the digital healthcare service recommendation engine 325 are provided in the examples which follow. The digital healthcare service recommendation engine 325 may be implemented in part by elements of the raw data layer 205, the event-based notification layer 250, and the insights layer 290 shown in FIG. 2.

The digital healthcare service provider information 305 may include information from the digital healthcare service providers 140 that indicates the types of services provided by the digital healthcare service providers 140. The digital healthcare service provider information may be obtained from the digital healthcare service providers 140 via the digital health service provider portal 160. In some implementations, at least some of the digital healthcare service providers may provide the digital healthcare service provider information via the digital health service provider API 295. The CAAS 105 may be configured to obtain digital healthcare service provider information 305 for a particular user for whom the benefits recommendations are to be provided. The recommendations may include recommendations for services from one or more digital healthcare service providers that may be covered by the employer and/or may save the employee user money compared to obtaining similar services through their insurance provider.

The digital healthcare service provider information 305 may be obtained by the digital health service provider API 295 of the raw data layer 205 shown in FIG. 2. The information obtained from each of the digital healthcare service providers may be in various electronic formats, including but not limited to Portable Document Format (PDF) or another electronic format supported by each digital health service provider. The information obtained from the digital healthcare service providers 140 may be stored in the data lake 210 of the raw data layer 205. The digital healthcare service provider parsing engine 315 may be configured to analyze the raw policy data obtained from the digital healthcare service providers and to convert the policy information to a standard schema. The standardized information may be stored in the digital health service provider benefits information 285. The standardized information may include information identifying the services provided by the digital health service provider, the costs associated with these services, the amount of these costs that may be covered by the user's employer, copay or deductible information, and/or other information that may be used by the CAAS 105 to determine whether the user may be able to reduce their healthcare costs by utilizing the services provided by one or more digital healthcare service providers 140. The policy information may also be used by the digital health service recommendation information 325 to provide guidance to the user in utilizing their available benefits.

The digital healthcare service provider parsing engine 315 may be configured to use fuzzy matching techniques to map information extracted from the digital healthcare service provider information to standardized benefits information. Digital healthcare service providers may use slightly different language to describe the services that they provide. The digital healthcare service provider parsing engine 315 may be configured to map the policy coverage information with a set of standardized service descriptions maintained by the CAAS 105. The standardized service descriptions may include descriptions of types of services that may be provided by the digital healthcare service providers 140. The digital healthcare service provider parsing engine 315 may be configured to perform a probabilistic data match on the service information provided by the digital healthcare service providers 140 with the standardized coverages descriptions. The digital healthcare service provider parsing engine 315 may be configured to select a standardized description that is associated with the highest probability of being a match with the service description. The matching standardized description may be stored in with the digital health service provider benefits information 285 and may be used by the digital healthcare service provider parsing engine 315 to provide recommendations to the user regarding services that may be subsidized in whole or in part by their employer.

Mapping the service information to standard descriptions may provide a significant technical benefit by improving the predictions that are provided by the machine learning models used by the digital healthcare service provider parsing engine 315. The machine learning models may be trained using training data that includes the same standard service descriptions that will be used by the digital healthcare service provider parsing engine 315 for providing recommendations and reminders to the insured user for utilizing their benefits. Thus, the machine learning models may be presented services information for analysis that utilizes descriptions consistent with the service descriptions included in the training data used to train the model or models.

The claims and prescription information 310 may include substantially real-time information from a medical claims feed and prescription feed. The medical claims information represents insurance claims that the user has submitted or has had submitted on their behalf for reimbursement. The prescription information represents prescriptions that have been prescribed to the user and may be submitted for reimbursement to an insurer. The claims and/or prescription information may be obtained by the claims and policy API 240 shown in FIG. 2 and the data stored in the data lake 210. The claims and prescription information obtained from each of the insurers may be in different electronic formats and/or layouts. The claims and prescription information may be processed by the claims and parsing engine 320 to convert the claims and prescription information into the standard schema utilized by the CAAS 105. The claims and prescription information in the standardized schema may be stored with the plan metadata 215.

The claims and prescription parsing engine 320 may be configured to use fuzzy matching techniques to map the claims and prescription information 310 to standardized claims and prescription descriptions before the claims and prescription information is analyzed by the claims and prescription parsing engine 320. Medical providers may use inconsistent language to describe the procedures performed. One medical provider may describe the same procedure in a slightly different way than another provider. Such inconsistencies in the description of the procedures performed can make determining whether a particular policy covers a particular claim or prescription. The set of standardized claim and prescription descriptions may provide a consistent set of descriptions that may be associated with claims and prescriptions. The claims and prescription parsing engine 320 may be configured to perform a probabilistic data match on the claims and prescription information 310 with the standardized claim and prescription descriptions. The claims and prescription parsing engine 320 may be configured to select a standardized description that is associated with the highest probability of being a match with the description of the procedure performed and/or other information included in the claim and/or prescriptions submitted to the insurer on behalf of a user.

The standardized description matched with a claim may be stored with the claim information in the plan metadata 215 associated with the claim. The standardized description may also be used by the CAAS 105 to determine whether one or more service providers provide services that are associated with one or more claims. The policy information may also be used by the digital healthcare service recommendation engine 325 to make recommendations to the user regarding services provided by the digital healthcare service providers 140. Mapping the claims and prescription information to standard descriptions provides the technical benefit of improving the predictions that are provided by the machine learning models used by the digital healthcare service recommendation engine 325. The machine learning models may be trained using training data that includes the same standard claim and/or prescription descriptions that will be used by the digital healthcare service recommendation engine 325 to make recommendations to the user for making better use of their benefits. Thus, the machine learning models are presented claims and prescription descriptions for analysis that utilizes descriptions consistent with the claims and prescription descriptions included in the training data used to train the models.

If the probability of the standardized description matching a particular claim is less than a predetermined threshold, the claims and prescription parsing engine 320 may flag the claim for additional processing. The user may be prompted to provide additional information that may be used to help disambiguate the claim and/or to request that a different description for the claim be provided. Standardizing the descriptions of the claims may increase the likelihood that the digital healthcare service provider information 305 may correctly analyze the claims and utilization to make recommendations to the user for utilizing their benefits.

The digital healthcare service recommendation engine 325 analyzes the information received from the digital healthcare service provider parsing engine 315 and the claims and prescription parsing engine 320 to provide various services that may include: (1) claims-based updates or alerts that include information that indicates that one or more services offered by the digital healthcare service providers 140 may save the user money by utilizing these services, (2) updates or alerts that identify one or more services offered by the digital healthcare service providers 140 that may be relevant to the user based on demographic information for the user, and (3) periodic savings reports that provide an analysis of the user's insurance-related activities and usage of services provided by the digital healthcare service providers 140 and estimated savings that have been or may have been achieve through the usage of these services.

Figure 4:
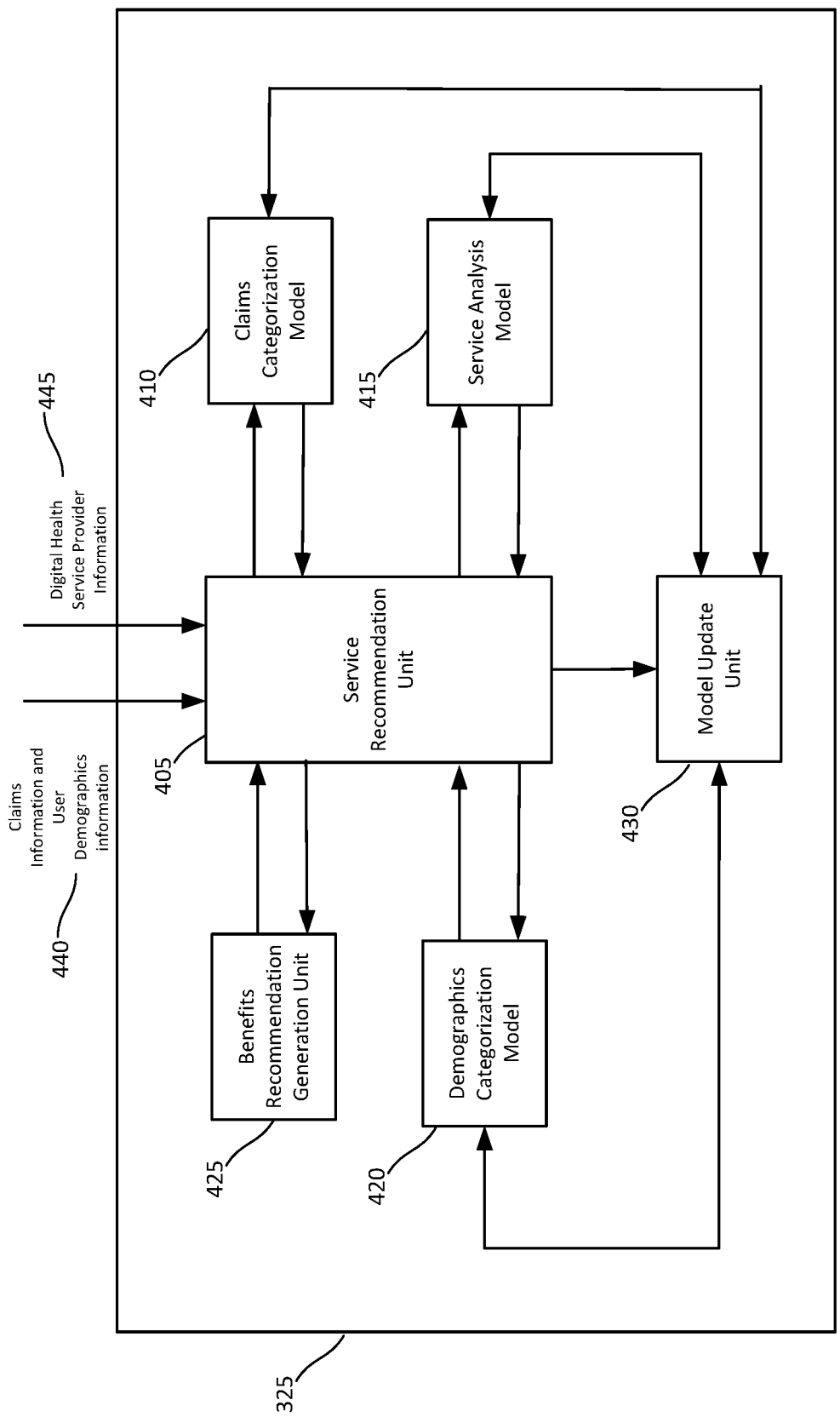
FIG. 4 is a diagram of an example architecture that shows additional details of the CAAS that may be used to implement the covered service recommendation engine shown in FIG. 3.

FIG. 4 is a diagram showing an example implementation of the digital healthcare service recommendation engine 325 of the CAAS 105. The digital healthcare service recommendation engine 325 may include a service recommendation unit 405, a claims categorization model 410, a service analysis model 415, a demographics categorization model 420, a benefit recommendation generation unit 425, and a model update unit 430. Other implementations may have a different configuration with a different number of machine learning models configured to support the recommendations for assisting the user in utilizing their benefits and insurance.

The digital healthcare service recommendation engine 325 may analyze user data from the various sources discussed above to provide recommendations for assisting the user in utilizing their benefits and insurance. Specifically, the digital healthcare service recommendation engine 325 may provide benefits recommendations 390 for services provided by the digital healthcare service providers 140 that are provided to the user through their employer. A recommendation may be generated on demand in response to a request from the user or automatically by the CAAS 105. The CAAS 105 may be configured to analyze the user data and generate the recommendations according to a schedule or in response to certain events.

The service recommendation unit 405 may be configured to obtain claims information and user demographic information 440 and digital healthcare service provider information 445 to be analyzed to provide various recommendations to the user for more fully utilizing their benefits. The claims information may include standardized claim and prescription information output by the claim and prescription parsing engine 320. The demographic information may also be standardized according to the standard schema. The demographic data may be collected from various sources, including the employer portal 150, the employee portal, and/or the third-party data providers 130. The digital healthcare service provider information 445 is the standardized digital search provider information output by the digital healthcare service provider parsing engine 315.

The service recommendation unit 405 may utilize the claims categorization model 410 to analyze the claims information and to identify a category associated with each of the claims. The claims categorization model 410 may be trained to categorize claims into a set of predetermined categories. The categories may correspond to a particular type of service that may be offered by one or more of the digital healthcare service providers 140. The data may be stored in the data lake 210 and/or in other memory locations by the raw data layer 205. The service recommendation unit 405 may utilize the predictions provided by claims categorization model 410 to generate the benefits recommendations 390. Examples of such recommendations are shown in the user interfaces 705 and 715 shown in FIGS. 7A and 7B.

The service recommendation unit 405 may utilize the demographics categorization model 420 to analyze the standardized user demographics information associated with the user to identify one or more categories of services that may benefit the user. The demographics categorization model 420 may be configured to determine one or more standard categories of service based on the demographic data of the user. For example, the demographic data may indicate that the user is female and has recently had a child. The demographics categorization model 420 may determine that the user may benefit from post-natal care services and may also benefit from sleep health related services. Other types of recommendations may be made for users based on their specific demographic data, and the demographics categorization model 420 may predict that the users may benefit from a set of services provided by the digital health care services providers 140.

The service recommendation unit 405 may be configured use the service analysis model 415 to predict which digital healthcare service providers 140 may provide services which are relevant to the user. The service analysis model 415 may be configured to receive as input the claim categories output by the claims categorization model 410, the category information output by the demographics categorization model 420, and/or the digital healthcare service provider information 445. The service analysis model 415 may predict that one or more service providers that provide services in the categories output by the claims categorization model 410 and/or the demographics categorization model 420. The digital healthcare service provider information 445 may include the standardized digital healthcare service provider information output by the digital healthcare service provider parsing engine 315 that identifies the digital healthcare service providers 140 with which the user's employer has contracted to provide services to its employees.

The service recommendation unit 405 may provide the recommended digital healthcare service providers to the benefits recommendation generation unit 425 which may generate the benefits recommendations 390. The benefits recommendations may identify the one or more digital healthcare service providers that the models of the digital healthcare service recommendation engine 325 have predicted may benefit the user. The benefit recommendations 390 may include information indicating why the recommendation for the particular service is being made to the user. The benefit recommendations 390 may also include predicted monetary savings that the user may experience by utilizing the digital health recommendation service (if applicable). For example, if the digital healthcare service recommendation engine 325 determined that the user had recent claims related to psychiatric treatment that were filed with the health insurance policy of the user, the digital healthcare service recommendation engine 325 may identify and present to the user one or more digital health care providers whose services are provided by the user's employer and that provide psychiatric and counseling services. The benefit recommendations 390 may include a cost savings associated with using each of the recommended digital health care services compared with the care provided under the health insurance of the user. The digital healthcare service providers may provide high quality care at a significantly lower cost than traditional providers. Furthermore, some patients may prefer to engage in remote care due to mobility issues, being located in a remote geographical location, or simply prefer to obtain care from the comfort of their own home.

The model update unit 430 may be configured to provide feedback to the claims categorization model 410 to refine the training of the model. The model update unit 430 may receive feedback directly from the user and/or from the service recommendation unit 405. Feedback from the user may be obtained from the service recommendation unit 405 in response to the user opting to not to select one or more recommendations to utilize benefits provided by the digital healthcare service providers 140. The feedback may be used to further refine the categories predicted by the claims categorization model 410 and/or the service recommendations provided by the service analysis model 415.

FIG. 5 shows an example user interface 505 that may be implemented by the digital health service provider portal 160. The user interface 505 is an example of a user interface that the CAAS 105 may present to a digital health service provider of the digital healthcare service providers 140 to guide the service provider through setting up an account on the CAAS 105 that enables the service provider to advertise their services to employers who may be interested in offering their services to the employer's employees. The data collected by the user interface 505 may be analyzed by the digital healthcare service provider parsing engine 315 to standardize the information provided by the digital health service provider.

The user interface 505 may guide the digital health service provider through a series of questions that collect information about the types of services provided by the digital health service provider. The questions may be dynamically generated by the digital health service provider portal 160 based on responses to previous questions. The information provided by the digital health service provider may be used to match the digital health service provider with employers seeking to provide the type of services offered by the digital health service provider and with employees who may benefit from such services.

FIGS. 6A, 6B, and 6C show example user interfaces 605, 610, and 615 that may be implemented by the employer portal 150. The user interface 605 may provide means for adding digital healthcare service providers for providing services to employees of the employer. The user interface 605 may guide the employer through a series of questions that regarding the types of services that the employer would like to provide for its employees. The user interface 610 is an example user interface for presenting details about a digital health service provider to the employer. The user interface 610 may include controls, which when activated, that enable the user to obtain further information about the service plans offered by the service provider, to connect with a representative of the digital health service provider to discuss the services provided, and/or to set up an agreement with the service provider to provide services to the employees. The information may include estimated costs to the employee for providing the services, estimated costs to the employees for the services provided, and/or estimated savings that may be achieved for the employees who utilize the services provided by the digital healthcare service provider. The user interface 615 shows a list of the digital healthcare service providers which the employer has contracted to provide services to the employer's employees and/or digital healthcare service providers that the has saved to a list of favorite providers for later reference. The user interface 615 may provide controls, which when activated, allow the employer to view the details of a particular digital health service provider on the user interface 610.

Figure 7A:

FIGS. 7A and 7B show example user interfaces 705 and 715 that may be implemented by the employee portal 155. The user interface 705 shows an example of an employee insurance a benefits dashboard where an employee user may access information about the insurance policies, claims and prescription information, and/or other benefits provided by the employer. The user interface 705 may include a benefits alert pane 710 for presenting updates or alerts to the user regarding benefits that are available to the user. The benefits alert pane 710 may include benefits provided by one or more digital healthcare service providers 140. The recommendations presented in the benefits alert pane 710 may include the benefits recommendations 390 generated by the digital healthcare service recommendation engine 325. The user may click on or otherwise select one of the alerts in the benefits alert pane 710 to view details about the digital health service provider associated with the selected benefits alert.

The user interface 715 shown in FIG. 7B provides details about a selected digital health service provider. The user interface 715 may include a control, which when activated, allows the user to get started setting up an account with and/or accessing the services provided by the digital health service provider. The user interface 715 may also include a control, which when activated, connects the user with a customer service representative that may provide additional information to the user and/or assist the user with their benefits.

Figure 8:
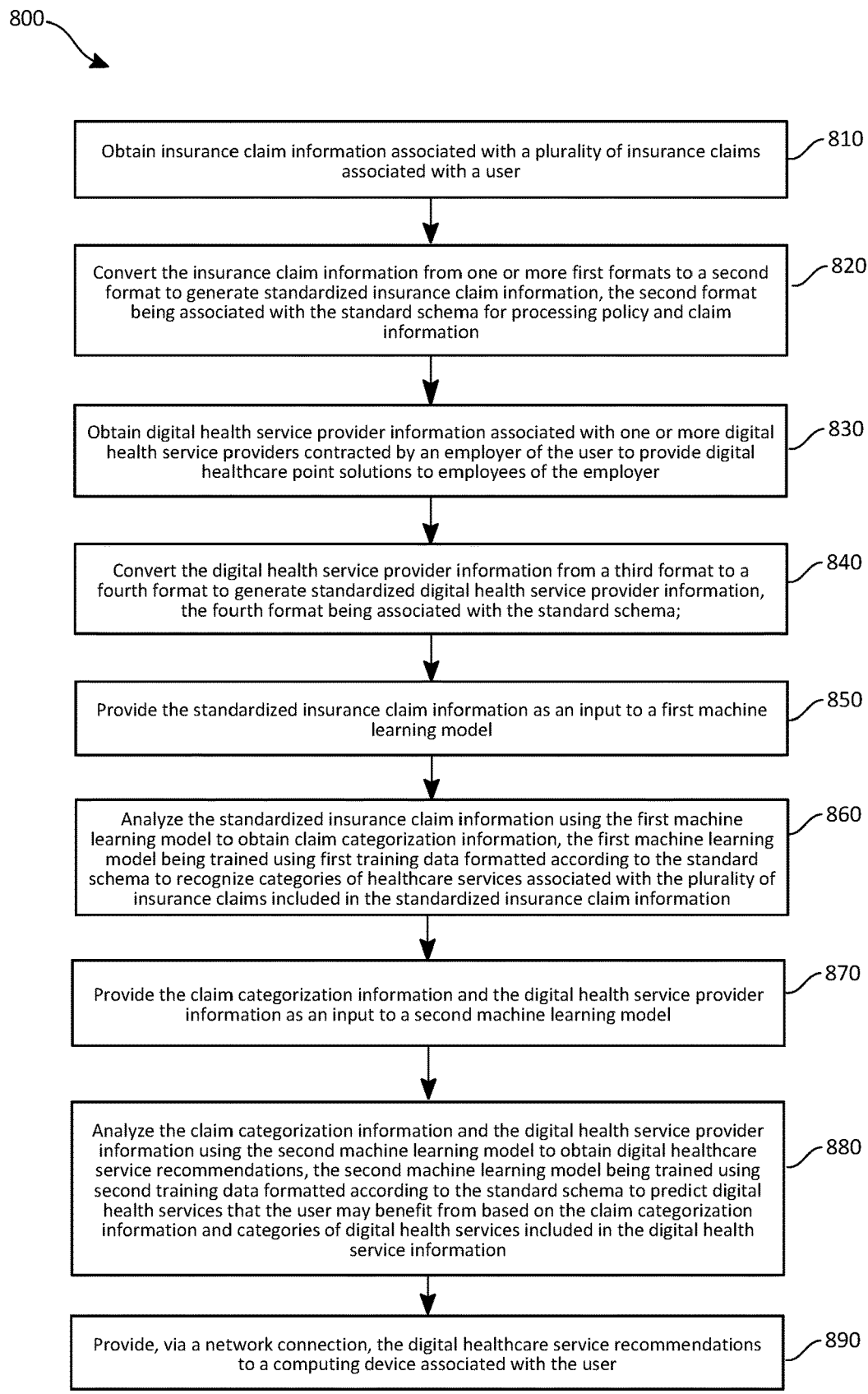
FIG. 8 a flow chart of an example process for recommending benefits from one or more digital healthcare service providers available to a user.

FIG. 8 a flow chart of an example process 800 for recommending benefits from one or more digital healthcare service providers available to a user. The process 800 may be implemented by the CAAS 105 discussed in the preceding examples.

The process 800 may include an operation 810 of obtaining insurance claim information associated with a plurality of insurance claims associated with a user. As discussed in the preceding examples, the demographic data may be collected from various sources, including the employer portal 150, the employee portal, and/or the third-party data providers 130. The CAAS 105 may collect the demographic information from the user by presenting a set of dynamically generated questions, and the demographic information may be stored in the census data 220 of the CAAS 105.

The process 800 may include an operation 820 of converting the insurance claim information from one or more first formats to a second format to generate standardized insurance claim information. The second format is associated with the standard schema for processing policy and claim information. The insurance claim information may be converted to the standard schema which was used to format the training data used to train the machine learning models used by the CAAS 105. This approach may significantly improve the predictions made by the machine learning models.

The process 800 may include an operation 830 of obtaining digital healthcare service provider information associated with one or more digital healthcare service providers contracted by an employer of the user to provide digital healthcare point solutions to employees of the employer. As discussed in the preceding examples, the digital healthcare service providers 140 may provide information about the services that they provide via the digital health service provider portal 160 and/or via the digital health service provider API 295.

The process 800 may include an operation 840 of converting the digital healthcare service provider information from a third format to a fourth format to generate standardized digital healthcare service provider information. The fourth format is associated with the standard schema. The digital healthcare service provider information may be converted to the standard schema to improve the predictions obtained from the machine learning models used by the CAAS 105.

The process 800 may include an operation 850 of providing the standardized insurance claim information as an input to a first machine learning model and an operation 860 of analyzing the standardized insurance claim information using the first machine learning model to obtain claim categorization information. The first machine learning model is trained using first training data formatted according to the standard schema to recognize categories of healthcare services associated with each insurance claim included in the standardized insurance claim information. The first machine learning model may be implemented by the claims categorization model 410 of the digital healthcare service recommendation engine 325.

The process 800 may include an operation 870 of providing the claim categorization information and the digital healthcare service provider information as an input to a second machine learning model, and an operation 880 of analyzing the claim categorization information and the digital healthcare service provider information using the second machine learning model to obtain digital healthcare service recommendations. The second machine learning model is trained using second training data formatted according to the standard schema to predict digital health services that the user may benefit from based on the claim categorization information and categories of digital health services included in the digital healthcare service provider information. The second machine learning model may be implemented by the service analysis model 415 of the digital healthcare service recommendation engine 325.

The process 800 may include an operation 890 of providing, via a network connection, the digital healthcare service recommendations to a computing device associated with the user. The digital healthcare service recommendation engine 325 may cause the user's client device 115 to display the benefits recommendations 390. As discussed in the preceding examples, the user may interact with the CAAS 105 via a native application associated with the CAAS 105 on the client device 115 or via a web browser on the client device 115. The recommendations associated with the available benefits may be presented to the user. Examples of the user interfaces that may be provided by the CAAS 105 for presenting this information to the user are shown in FIGS. 7A and 7B.

Figure 9:
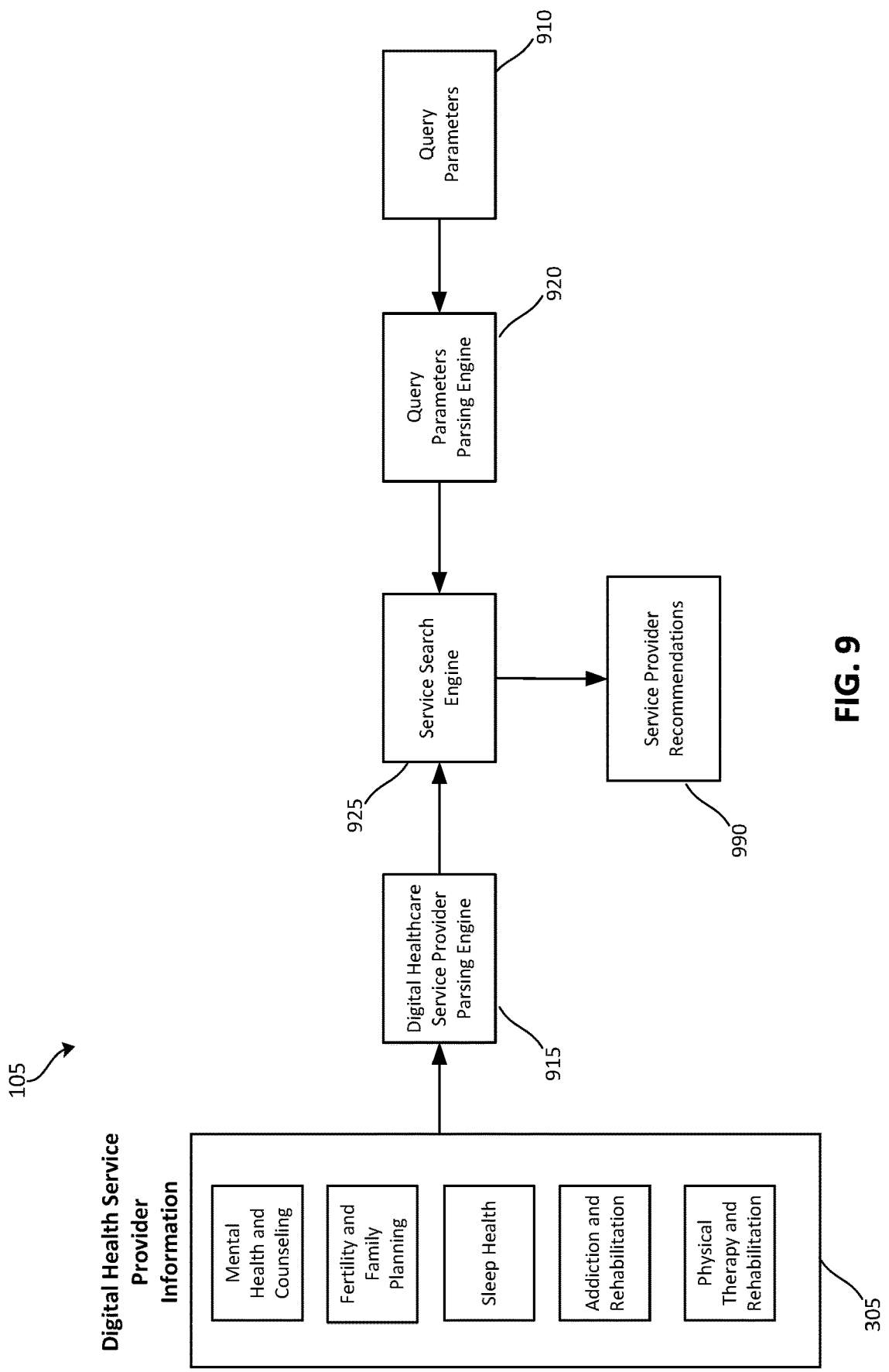
FIG. 9 is a diagram that shows an example implementation of a search service engine that may be implemented by the CAAS.

FIG. 9 is a diagram that shows an example implementation of a search service engine 925 that may be implemented by the CAAS 105. The search service engine 925 may be configured to provide machine-learning driven recommendations for assisting an employer in searching for benefits provided by one or more digital healthcare service providers. The search service engine 925 may provide recommendations based on the query parameters entered by the user via the user interface 605 shown in FIG. 6A. The query parameters may define characteristics of the types of services for which the employer is searching for service providers which may provide digital health care services to the employer's employees. The search service engine 925 may be implemented in part by elements of the raw data layer 205, the event-based notification layer 250, and the insights layer 290 shown in FIG. 2.

The search service engine 925 may utilize the standardized digital healthcare service provider information output by the digital service provider parsing engine 915. The digital healthcare service provider information 1045 may include standardized digital healthcare service provider information output by the digital healthcare service provider parsing engine 915. The digital healthcare service provider information 1045 identifies digital healthcare service providers 140 with which employer may contract to provide services to its employees. The search service engine 925 may also utilize standardized query parameters output by the query parameters parsing engine 920. The query parameters parsing engine 920 may receive query parameters 910 provided by an employer searching for digital healthcare service providers that may provide services to the employees of the employer. The search service engine 925 may output service provider recommendations 990, which may be presented on the client device 115 of the employer.

Figure 10:
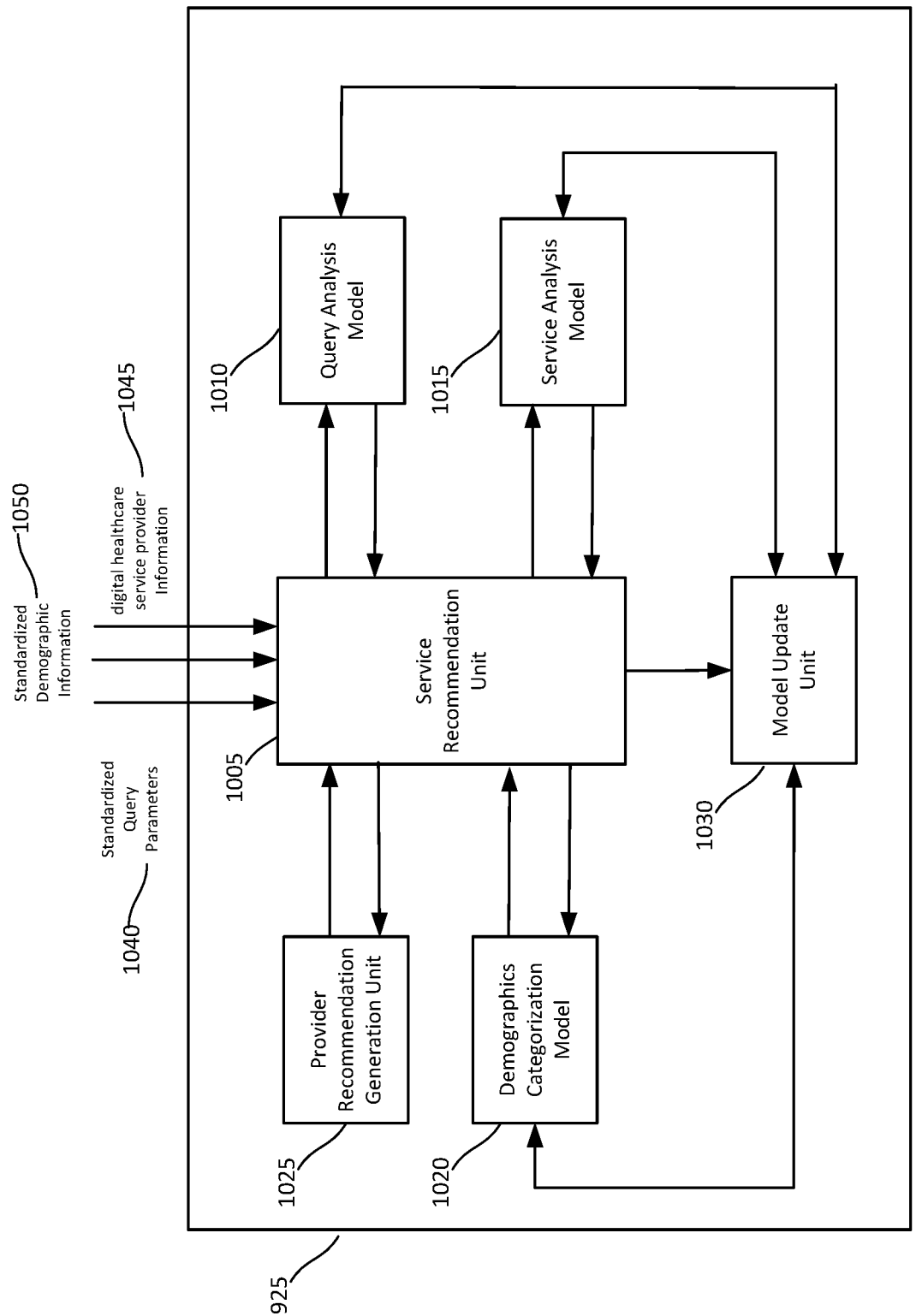
FIG. 10 is a diagram showing an example implementation of the search service engine of the CAAS.

FIG. 10 is a diagram showing an example implementation of the search service engine 925 of the CAAS 105. The search service engine 925 may include a service recommendation unit 1005, a query analysis model 1010, a service analysis model 1015, a demographics categorization model 1020, a provider recommendation generation unit 1025, and a model update unit 1030. Other implementations may have a different configuration with a different number of machine learning models configured to support the recommendations for assisting the employer in selecting digital healthcare service providers to provide benefits for the employer's employees.

The service recommendation unit 1005 may be configured to obtain standardized query parameters 1040 and digital healthcare service provider information 1045 to be analyzed to provide recommendations to the employer for digital healthcare service providers that may provide benefits to their employers. The standardized query parameters 1040 may include query parameters formatting according to the standard schema and output by the query parameters parsing engine 920. The digital healthcare service provider information 1045 is the standardized digital search provider information output by the digital healthcare service provider parsing engine 915.

The service recommendation unit 1005 may utilize the query analysis model 1010 to analyze the standardized query parameters 1040 to predict a category or categories of services associated with the query parameters provided by employer. The query analysis model 1010 may be trained to categorize the query parameters into a set of predetermined categories. The categories may correspond to a particular type of service that may be offered by one or more of the digital healthcare service providers 140 and included in the digital healthcare service provider information 1045. The data may be stored in the data lake 210 and/or in other memory locations by the raw data layer 205.

The service recommendation unit 1005 may utilize standardized demographic information 1050 for the employees in addition to or instead of the query parameters provided by the employer to determine categories of services provided by the digital healthcare service provider 140 that may be relevant to the employees of the employer. The demographic information used to obtain digital healthcare service providers may be an aggregate of the demographic information for many employees rather than an individual employee. The aggregate information may be obtained by the service recommendation unit 1005 from the census data 220 of the CAAS 105. The demographic information may be standardized into the standard schema used to format the training data used to train the demographics categorization model 1020. As discussed in the preceding examples, the CAAS 105 may collect demographic information from the users. Some demographic information may also be provided by the employer.

The service recommendation unit 1005 may utilize the demographics categorization model 1020 to analyze the standardized user demographics information associated with the employees to identify one or more categories of services that may benefit the employees. The demographics categorization model 1020 may be configured to determine one or more standard categories of service based on the demographic data of the employees. The demographics categorization model 1020 may be similar to the demographics categorization model 420 shown in FIG. 4 and may predict that the employees may benefit from a set of services provided by the digital health care services providers 140.

The service recommendation unit 1005 may be configured use the service analysis model 1015 to predict which digital healthcare service providers 140 may provide services which are relevant to the employees of the employer. The service analysis model 1015 may be configured to receive as input the category information output by the query analysis model 1010, the category information output by the demographics categorization model 1020, and/or the digital healthcare service provider information 1045. The service analysis model 1015 may predict that one or more service providers that provide services in the categories output by the query analysis model 1010 and/or the demographics categorization model 1020. The digital healthcare service provider information 1045 may include the standardized digital healthcare service provider information output by the digital healthcare service provider parsing engine 915 that identifies the digital healthcare service providers 140 who may provide digital healthcare services to the employees of the employer.

The service recommendation unit 1005 may provide the recommended digital healthcare service providers output by the service analysis model 1015 to the provider recommendation generation unit 1025 which may generate the service provider recommendations 990. The service provider recommendations 990 may identify the one or more digital healthcare service providers that the service analysis model 1015 predicted may provide the types of services that the employer is seeking to provide for its employees. The service provider recommendations 990 may include information indicating why the recommendation for the particular service provider is being made to the employer. The service provider recommendations 990 may also include predicted monetary savings that the employees may experience by utilizing the digital health recommendation service. The digital healthcare service providers may provide high quality care at a significantly lower cost than traditional providers.

The model update unit 1030 may be configured to provide feedback to the query analysis model 1010 and the service analysis model 1015 to refine the training of the models. The model update unit 1030 may receive feedback directly from the user and/or from the service recommendation unit 1005. Feedback from the user may be obtained from the service recommendation unit 1005 in response to the user opting to not to select one or more recommendations to utilize benefits provided by the digital healthcare service providers 140. The feedback may be used to further refine the categories predicted by the query analysis model 1010 and/or the service analysis model 1015.

Figure 11:
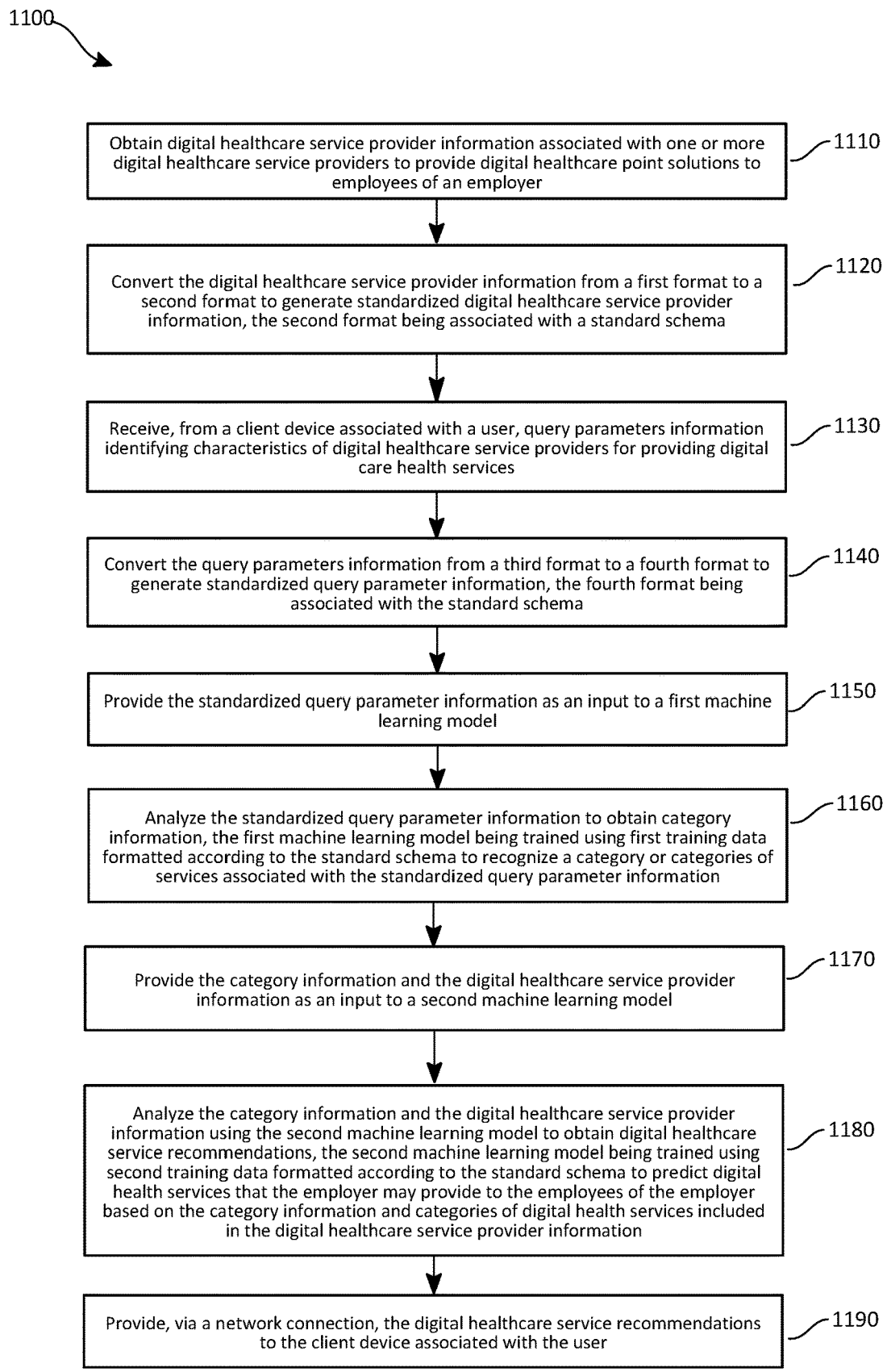
FIG. 11 a flow chart of an example process for recommending benefits from one or more digital healthcare service providers available to an employer.

FIG. 11 a flow chart of an example process 1100 for recommending benefits from one or more digital healthcare service providers available to an employer. The process 1100 may be implemented by the CAAS 105 discussed in the preceding examples.

The process 1100 may include an operation 1110 of obtaining digital healthcare service provider information associated with one or more digital healthcare service providers to provide digital healthcare point solutions to employees of an employer. As discussed in the preceding examples, the digital healthcare service providers 140 may provide information about the services that they provide via the digital health service provider portal 160 and/or via the digital health service provider API 295.

The process 1100 may include an operation 1120 of converting the digital healthcare service provider information from a first format to a second format to generate standardized digital healthcare service provider information. The second format is associated with the standard schema. The digital healthcare service provider information may be converted to the standard schema to improve the predictions obtained from the machine learning models used by the CAAS 105.

The process 1100 may include an operation 1130 of receiving, from a client device 115 associated with a user, query parameters information identifying characteristics of digital healthcare service providers for providing digital care health services. The user may provide the query parameters via a user interface similar to that show in FIG. 6A.

The process 1100 may include an operation 1140 of converting the query parameters information from a third format to a fourth format to generate standardized query parameter information. The fourth format being associated with the standard schema. The digital healthcare service provider information may be converted to the standard schema to improve the predictions obtained from the machine learning models used by the CAAS 105.

The process 1100 may include an operation 1150 of providing the standardized query parameter information as an input to a first machine learning model and an operation 1160 of analyzing the standardized query parameter information to obtain category information. The first machine learning model, which may be implemented by the query analysis model 10101, is trained using first training data formatted according to the standard schema to recognize a category or categories of services associated with the standardized query parameter information.

The process 1100 may include an operation 1170 of providing the category information and the digital healthcare service provider information as an input to a second machine learning model and an operation 1180 of analyzing the category information and the digital healthcare service provider information using the second machine learning model to obtain digital healthcare service recommendations. The second machine learning model, which may be implemented by the service analysis model 1015, is trained using second training data formatted according to the standard schema to predict digital health services that the employer may provide to the employees of the employer based on the category information and categories of digital health services included in the digital healthcare service provider information.

The process 1100 may include an operation 1190 of providing, via a network connection, the digital healthcare service recommendations to the client device 115 associated with the user. The digital healthcare service recommendation engine 325 may cause the user's client device 115 to display the benefits recommendations 390. As discussed in the preceding examples, the user may interact with the CAAS 105 via a native application associated with the CAAS 105 on the client device 115 or via a web browser on the client device 115. The recommendations associated with the available benefits that the employer may elect to provide to their employees may be presented to the user. Examples of the user interfaces that may be provided by the CAAS 105 for presenting this information to the user are shown in FIGS. 6B and 6C.

The detailed examples of systems, devices, and techniques described in connection with FIGS. 1-11 are presented herein for illustration of the disclosure and its benefits. Such examples of use should not be construed to be limitations on the logical process embodiments of the disclosure, nor should variations of user interface methods from those described herein be considered outside the scope of the present disclosure. It is understood that references to displaying or presenting an item (such as, but not limited to, presenting an image on a display device, presenting audio via one or more loudspeakers, and/or vibrating a device) include issuing instructions, commands, and/or signals causing, or reasonably expected to cause, a device or system to display or present the item. In some embodiments, various features described in FIGS. 1-11 are implemented in respective modules, which may also be referred to as, and/or include, logic, components, units, and/or mechanisms. Modules may constitute either software modules (for example, code embodied on a machine-readable medium) or hardware modules.

In some examples, a hardware module may be implemented mechanically, electronically, or with any suitable combination thereof. For example, a hardware module may include dedicated circuitry or logic that is configured to perform certain operations. For example, a hardware module may include a special-purpose processor, such as a field-programmable gate array (FPGA) or an Application Specific Integrated Circuit (ASIC). A hardware module may also include programmable logic or circuitry that is temporarily configured by software to perform certain operations and may include a portion of machine-readable medium data and/or instructions for such configuration. For example, a hardware module may include software encompassed within a programmable processor configured to execute a set of software instructions. It will be appreciated that the decision to implement a hardware module mechanically, in dedicated and permanently configured circuitry, or in temporarily configured circuitry (for example, configured by software) may be driven by cost, time, support, and engineering considerations.

Accordingly, the phrase "hardware module" should be understood to encompass a tangible entity capable of performing certain operations and may be configured or arranged in a certain physical manner, be that an entity that is physically constructed, permanently configured (for example, hardwired), and/or temporarily configured (for example, programmed) to operate in a certain manner or to perform certain operations described herein. As used herein, "hardware-implemented module" refers to a hardware module. Considering examples in which hardware modules are temporarily configured (for example, programmed), each of the hardware modules need not be configured or instantiated at any one instance in time. For example, where a hardware module includes a programmable processor configured by software to become a special-purpose processor, the programmable processor may be configured as respectively different special-purpose processors (for example, including different hardware modules) at different times. Software may accordingly configure a processor or processors, for example, to constitute a particular hardware module at one instance of time and to constitute a different hardware module at a different instance of time. A hardware module implemented using one or more processors may be referred to as being "processor implemented" or "computer implemented."

Hardware modules can provide information to, and receive information from, other hardware modules. Accordingly, the described hardware modules may be regarded as being communicatively coupled. Where multiple hardware modules exist contemporaneously, communications may be achieved through signal transmission (for example, over appropriate circuits and buses) between or among two or more of the hardware modules. In embodiments in which multiple hardware modules are configured or instantiated at different times, communications between such hardware modules may be achieved, for example, through the storage and retrieval of information in memory devices to which the multiple hardware modules have access. For example, one hardware module may perform an operation and store the output in a memory device, and another hardware module may then access the memory device to retrieve and process the stored output.

In some examples, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by, and/or among, multiple computers (as examples of machines including processors), with these operations being accessible via a network (for example, the Internet) and/or via one or more software interfaces (for example, an application program interface (API)). The performance of certain of the operations may be distributed among the processors, not only residing within a single machine, but deployed across several machines. Processors or processor-implemented modules may be in a single geographic location (for example, within a home or office environment, or a server farm), or may be distributed across multiple geographic locations.

Figure 12:
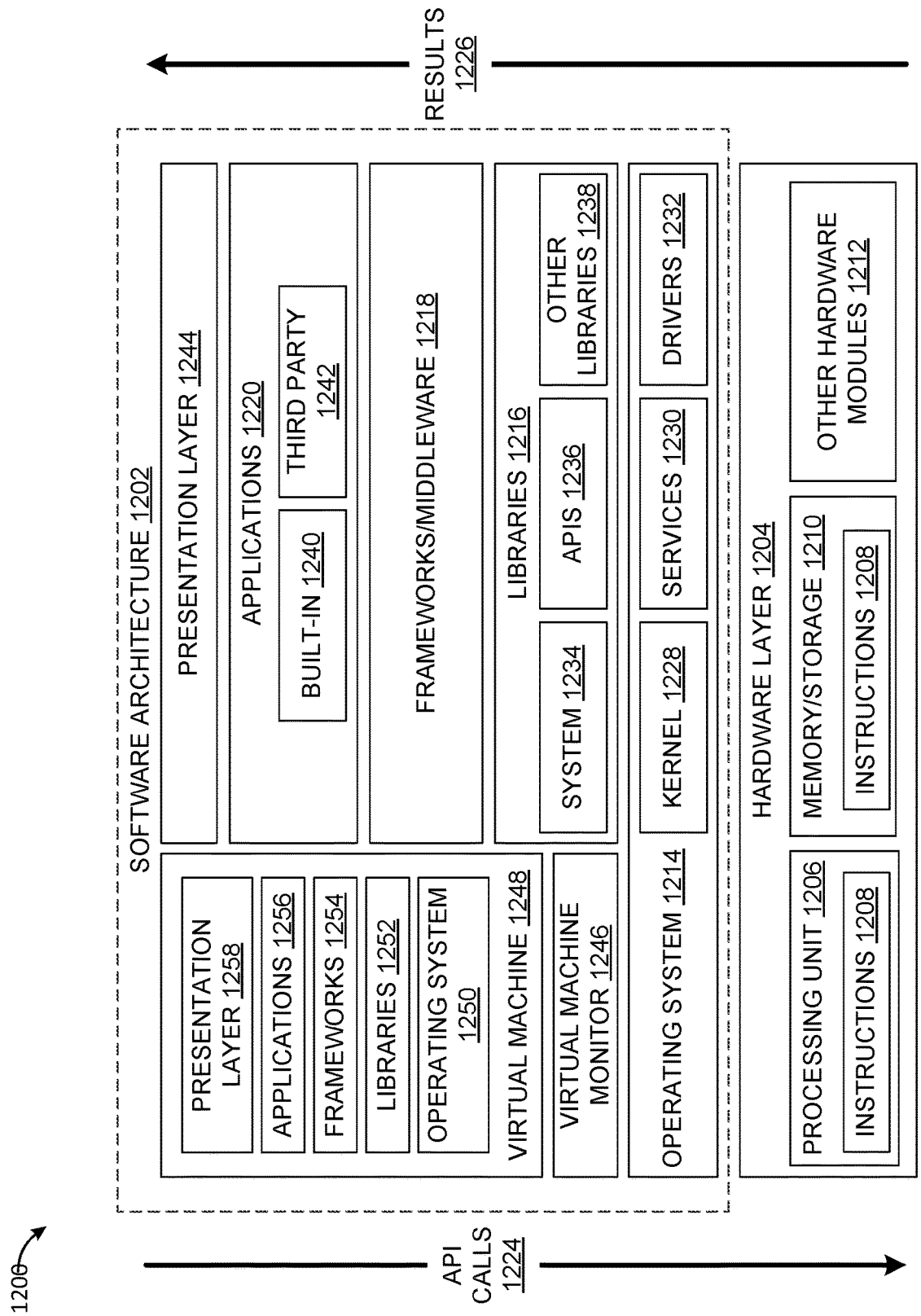
FIG. 12 is a block diagram showing an example software architecture, various portions of which may be used in conjunction with various hardware architectures herein described, which may implement any of the described features.

FIG. 12 is a block diagram 1200 illustrating an example software architecture 1202, various portions of which may be used in conjunction with various hardware architectures herein described, which may implement any of the above-described features. FIG. 12 is a non-limiting example of a software architecture, and it will be appreciated that many other architectures may be implemented to facilitate the functionality described herein. The software architecture 1202 may execute on hardware such as a machine 1300 of FIG. 13 that includes, among other things, processors 1310, memory 1330, and input/output (I/O) components 1350. A representative hardware layer 1204 is illustrated and can represent, for example, the machine 1300 of FIG. 13. The representative hardware layer 1204 includes a processing unit 1206 and associated executable instructions 1208. The executable instructions 1208 represent executable instructions of the software architecture 1202, including implementation of the methods, modules and so forth described herein. The hardware layer 1204 also includes a memory/storage 1210, which also includes the executable instructions 1208 and accompanying data. The hardware layer 1204 may also include other hardware modules 1212. Instructions 1208 held by processing unit 1206 may be portions of instructions 1208 held by the memory/storage 1210.

The example software architecture 1202 may be conceptualized as layers, each providing various functionality. For example, the software architecture 1202 may include layers and components such as an operating system (OS) 1214, libraries 1216, frameworks 1218, applications 1220, and a presentation layer 1244. Operationally, the applications 1220 and/or other components within the layers may invoke API calls 1224 to other layers and receive corresponding results 1226. The layers illustrated are representative in nature and other software architectures may include additional or different layers. For example, some mobile or special purpose operating systems may not provide the frameworks/middleware 1218.

The OS 1214 may manage hardware resources and provide common services. The OS 1214 may include, for example, a kernel 1228, services 1230, and drivers 1232. The kernel 1228 may act as an abstraction layer between the hardware layer 1204 and other software layers. For example, the kernel 1228 may be responsible for memory management, processor management (for example, scheduling), component management, networking, security settings, and so on. The services 1230 may provide other common services for the other software layers. The drivers 1232 may be responsible for controlling or interfacing with the underlying hardware layer 1204. For instance, the drivers 1232 may include display drivers, camera drivers, memory/storage drivers, peripheral device drivers (for example, via Universal Serial Bus (USB)), network and/or wireless communication drivers, audio drivers, and so forth depending on the hardware and/or software configuration.

The libraries 1216 may provide a common infrastructure that may be used by the applications 1220 and/or other components and/or layers. The libraries 1216 typically provide functionality for use by other software modules to perform tasks, rather than rather than interacting directly with the OS 1214. The libraries 1216 may include system libraries 1234 (for example, C standard library) that may provide functions such as memory allocation, string manipulation, file operations. In addition, the libraries 1216 may include API libraries 1236 such as media libraries (for example, supporting presentation and manipulation of image, sound, and/or video data formats), graphics libraries (for example, an OpenGL library for rendering 2D and 3D graphics on a display), database libraries (for example, SQLite or other relational database functions), and web libraries (for example, WebKit that may provide web browsing functionality). The libraries 1216 may also include a wide variety of other libraries 1238 to provide many functions for applications 1220 and other software modules.

The frameworks 1218 (also sometimes referred to as middleware) provide a higher-level common infrastructure that may be used by the applications 1220 and/or other software modules. For example, the frameworks 1218 may provide various graphic user interface (GUI) functions, high-level resource management, or high-level location services. The frameworks 1218 may provide a broad spectrum of other APIs for applications 1220 and/or other software modules.

The applications 1220 include built-in applications 1240 and/or third-party applications 1242. Examples of built-in applications 1240 may include, but are not limited to, a contacts application, a browser application, a location application, a media application, a messaging application, and/or a game application. Third-party applications 1242 may include any applications developed by an entity other than the vendor of the particular platform. The applications 1220 may use functions available via OS 1214, libraries 1216, frameworks 1218, and presentation layer 1244 to create user interfaces to interact with users.

Some software architectures use virtual machines, as illustrated by a virtual machine 1248. The virtual machine 1248 provides an execution environment where applications/modules can execute as if they were executing on a hardware machine (such as the machine 1300 of FIG. 13, for example). The virtual machine 1248 may be hosted by a host OS (for example, OS 1214) or hypervisor, and may have a virtual machine monitor 1246 which manages operation of the virtual machine 1248 and interoperation with the host operating system. A software architecture, which may be different from software architecture 1202 outside of the virtual machine, executes within the virtual machine 1248 such as an OS 1250, libraries 1252, frameworks 1254, applications 1256, and/or a presentation layer 1258.

Figure 13:
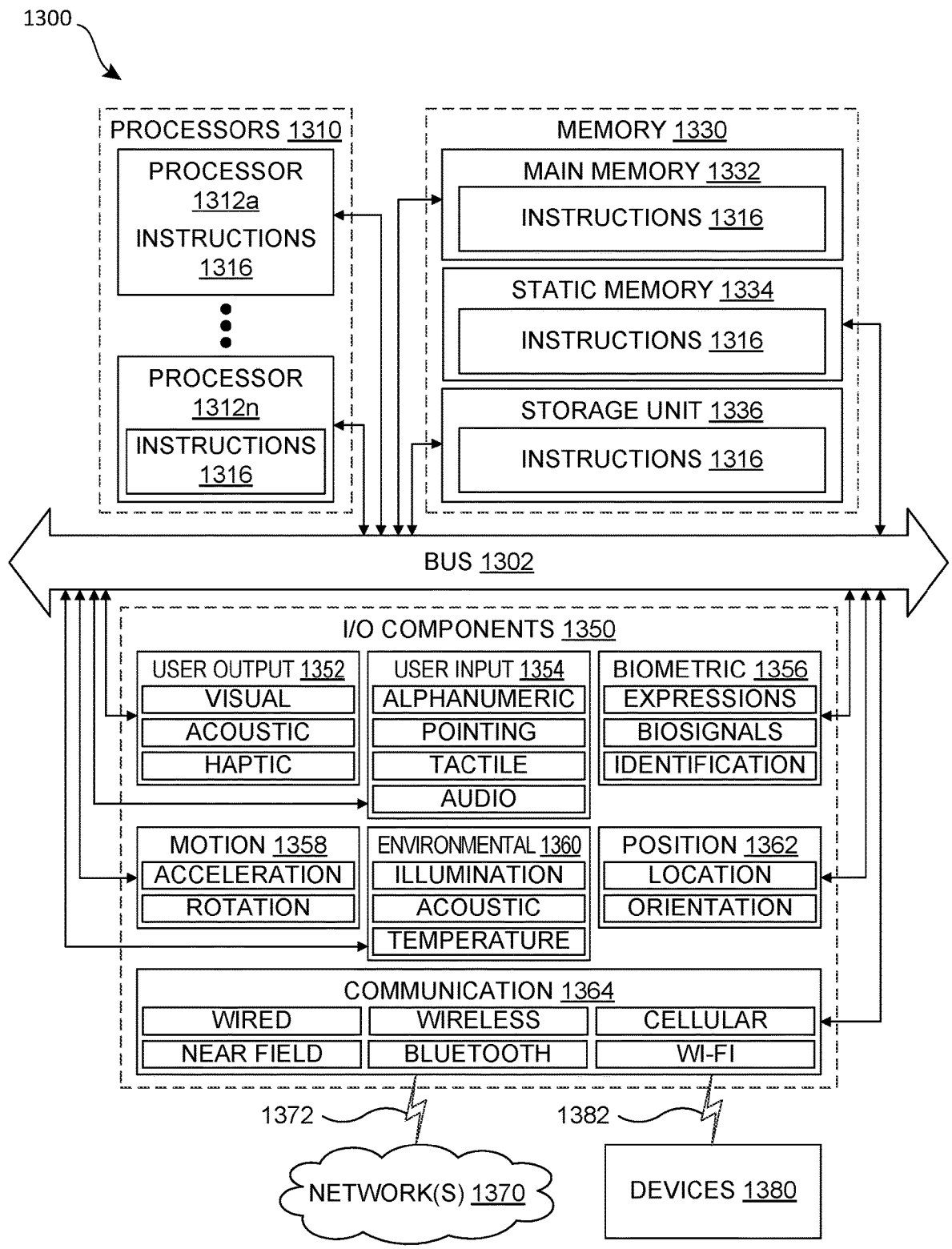
FIG. 13 is a block diagram showing components of an example machine configured to read instructions from a machine-readable medium and perform any of the features described herein.

FIG. 13 is a block diagram illustrating components of an example machine 1300 configured to read instructions from a machine-readable medium (for example, a machine-readable storage medium) and perform any of the features described herein. The example machine 1300 is in a form of a computer system, within which instructions 1316 (for example, in the form of software components) for causing the machine 1300 to perform any of the features described herein may be executed. As such, the instructions 1316 may be used to implement modules or components described herein. The instructions 1316 cause unprogrammed and/or unconfigured machine 1300 to operate as a particular machine configured to carry out the described features. The machine 1300 may be configured to operate as a standalone device or may be coupled (for example, networked) to other machines. In a networked deployment, the machine 1300 may operate in the capacity of a server machine or a client machine in a server-client network environment, or as a node in a peer-to-peer or distributed network environment. Machine 1300 may be embodied as, for example, a server computer, a client computer, a personal computer (PC), a tablet computer, a laptop computer, a netbook, a set-top box (STB), a gaming and/or entertainment system, a smart phone, a mobile device, a wearable device (for example, a smart watch), and an Internet of Things (IoT) device. Further, although only a single machine 1300 is illustrated, the term "machine" includes a collection of machines that individually or jointly execute the instructions 1316.

The machine 1300 may include processors 1310, memory 1330, and I/O components 1350, which may be communicatively coupled via, for example, a bus 1302. The bus 1302 may include multiple buses coupling various elements of machine 1300 via various bus technologies and protocols. In an example, the processors 1310 (including, for example, a central processing unit (CPU), a graphics processing unit (GPU), a digital signal processor (DSP), an ASIC, or a suitable combination thereof) may include one or more processors 1312a to 1312n that may execute the instructions 1316 and process data. In some examples, one or more processors 1310 may execute instructions provided or identified by one or more other processors 1310. The term "processor" includes a multi-core processor including cores that may execute instructions contemporaneously. Although FIG. 13 shows multiple processors, the machine 1300 may include a single processor with a single core, a single processor with multiple cores (for example, a multi-core processor), multiple processors each with a single core, multiple processors each with multiple cores, or any combination thereof. In some examples, the machine 1300 may include multiple processors distributed among multiple machines.

The memory/storage 1330 may include a main memory 1332, a static memory 1334, or other memory, and a storage unit 1336, both accessible to the processors 1310 such as via the bus 1302. The storage unit 1336 and memory 1332, 1334 store instructions 1316 embodying any one or more of the functions described herein. The memory/storage 1330 may also store temporary, intermediate, and/or long-term data for processors 1310. The instructions 1316 may also reside, completely or partially, within the memory 1332, 1334, within the storage unit 1336, within at least one of the processors 1310 (for example, within a command buffer or cache memory), within memory at least one of I/O components 1350, or any suitable combination thereof, during execution thereof. Accordingly, the memory 1332, 1334, the storage unit 1336, memory in processors 1310, and memory in I/O components 1350 are examples of machine-readable media.

As used herein, "machine-readable medium" refers to a device able to temporarily or permanently store instructions and data that cause machine 1300 to operate in a specific fashion, and may include, but is not limited to, random-access memory (RAM), read-only memory (ROM), buffer memory, flash memory, optical storage media, magnetic storage media and devices, cache memory, network-accessible or cloud storage, other types of storage and/or any suitable combination thereof. The term "machine-readable medium" applies to a single medium, or combination of multiple media, used to store instructions (for example, instructions 1316) for execution by a machine 1300 such that the instructions, when executed by one or more processors 1310 of the machine 1300, cause the machine 1300 to perform and one or more of the features described herein. Accordingly, a "machine-readable medium" may refer to a single storage device, as well as "cloud-based" storage systems or storage networks that include multiple storage apparatus or devices. The term "machine-readable medium" excludes signals per se.

The I/O components 1350 may include a wide variety of hardware components adapted to receive input, provide output, produce output, transmit information, exchange information, capture measurements, and so on. The specific I/O components 1350 included in a particular machine will depend on the type and/or function of the machine. For example, mobile devices such as mobile phones may include a touch input device, whereas a headless server or IoT device may not include such a touch input device. The particular examples of I/O components illustrated in FIG. 13 are in no way limiting, and other types of components may be included in machine 1300. The grouping of I/O components 1350 are merely for simplifying this discussion, and the grouping is in no way limiting. In various examples, the I/O components 1350 may include user output components 1352 and user input components 1354. User output components 1352 may include, for example, display components for displaying information (for example, a liquid crystal display (LCD) or a projector), acoustic components (for example, speakers), haptic components (for example, a vibratory motor or force-feedback device), and/or other signal generators. User input components 1354 may include, for example, alphanumeric input components (for example, a keyboard or a touch screen), pointing components (for example, a mouse device, a touchpad, or another pointing instrument), and/or tactile input components (for example, a physical button or a touch screen that provides location and/or force of touches or touch gestures) configured for receiving various user inputs, such as user commands and/or selections.

In some examples, the I/O components 1350 may include biometric components 1356, motion components 1358, environmental components 1360, and/or position components 1362, among a wide array of other physical sensor components. The biometric components 1356 may include, for example, components to detect body expressions (for example, facial expressions, vocal expressions, hand or body gestures, or eye tracking), measure biosignals (for example, heart rate or brain waves), and identify a person (for example, via voice-, retina-, fingerprint-, and/or facial-based identification). The motion components 1358 may include, for example, acceleration sensors (for example, an accelerometer) and rotation sensors (for example, a gyroscope). The environmental components 1360 may include, for example, illumination sensors, temperature sensors, humidity sensors, pressure sensors (for example, a barometer), acoustic sensors (for example, a microphone used to detect ambient noise), proximity sensors (for example, infrared sensing of nearby objects), and/or other components that may provide indications, measurements, or signals corresponding to a surrounding physical environment. The position components 1362 may include, for example, location sensors (for example, a Global Position System (GPS) receiver), altitude sensors (for example, an air pressure sensor from which altitude may be derived), and/or orientation sensors (for example, magnetometers).

The I/O components 1350 may include communication components 1364, implementing a wide variety of technologies operable to couple the machine 1300 to network(s) 1370 and/or device(s) 1380 via respective communicative couplings 1372 and 1382. The communication components 1364 may include one or more network interface components or other suitable devices to interface with the network(s) 1370. The communication components 1364 may include, for example, components adapted to provide wired communication, wireless communication, cellular communication, Near Field Communication (NFC), Bluetooth communication, Wi-Fi, and/or communication via other modalities. The device(s) 1380 may include other machines or various peripheral devices (for example, coupled via USB).

In some examples, the communication components 1364 may detect identifiers or include components adapted to detect identifiers. For example, the communication components 1364 may include Radio Frequency Identification (RFID) tag readers, NFC detectors, optical sensors (for example, one- or multi-dimensional bar codes, or other optical codes), and/or acoustic detectors (for example, microphones to identify tagged audio signals). In some examples, location information may be determined based on information from the communication components 1362, such as, but not limited to, geo-location via Internet Protocol (IP) address, location via Wi-Fi, cellular, NFC, Bluetooth, or other wireless station identification and/or signal triangulation.

While various embodiments have been described, the description is intended to be exemplary, rather than limiting, and it is understood that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claims require more features than are expressly recited in each claim. Rather, as the following claims reflect, inventive subject matter lies in less than all features of a single disclosed example. Thus, the following claims are hereby incorporated into the Detailed Description, with each claim standing on its own as a separately claimed subject matter.

What is claimed is:

1. A data processing system comprising:
   a processor; and
   a machine-readable medium storing executable instructions that, when executed, cause the processor to perform operations comprising:
      obtaining digital healthcare service provider information associated with one or more digital healthcare service providers to provide digital healthcare point solutions to employees of an employer;
      converting the digital healthcare service provider information from a first format to a second format to generate standardized digital healthcare service provider information, the second format being associated with a standard schema;
      receiving, from a client device associated with a user, query parameters information identifying characteristics of digital healthcare service providers for providing digital care health services;
      converting the query parameters information from a third format to a fourth format to generate standardized query parameter information, the fourth format being associated with the standard schema;
      providing the standardized query parameter information as an input to a first machine learning model;
      analyzing the standardized query parameter information to obtain category information, the first machine learning model being trained using first training data formatted according to the standard schema to recognize a category or categories of services associated with the standardized query parameter information;
      providing the category information and the digital healthcare service provider information as an input to a second machine learning model;
      analyzing the category information and the digital healthcare service provider information using the second machine learning model to obtain digital healthcare service recommendations, the second machine learning model being trained using second training data formatted according to the standard schema to predict digital health services that the employer may provide to the employees of the employer based on the category information and categories of digital health services included in the digital healthcare service provider information; and
      providing, via a network connection, the digital healthcare service recommendations to the client device associated with the user.

2. The data processing system of claim 1, wherein the machine-readable medium includes instructions configured to cause the processor to perform operations of:
   obtaining an electronic copy of demographic information associated with the employees of the employer; and
   converting the demographic information from a third format to a fourth format to generate standardized demographic information, the fourth format being associated with the standard schema.

3. The data processing system of claim 2, wherein the machine-readable medium includes instructions configured to cause the processor to perform operations of:

providing the standardized demographic information as an input to a third machine learning model;

analyzing the standardized demographic information using the third machine learning model to obtain additional category information, the third machine learning model being trained using third training data formatted according to the standard schema to predict categories of healthcare services that may be relevant to the employees of the employer based on the standardized demographic information; and providing the category information, the additional claim category information, and the digital healthcare service provider information as an input to a second machine learning model.

4. The data processing system of claim 1, wherein the machine-readable medium includes instructions configured to cause the processor to perform an operation of:

causing to be displayed on the computing device associated with the user an employer dashboard user interface that includes a representation of the digital healthcare service recommendations.

5. The data processing system of claim 4, wherein the representation of the digital healthcare service recommendations includes controls, which when activated, establish a connection with a server of a respective digital health service provider to obtain services for the employees of the user.

6. The data processing system of claim 4, wherein the machine-readable medium includes instructions configured to cause the processor to perform an operation of:

causing the user device to display a user interface that guides the user through a process of setting up a contract with the respective digital health service provider.

7. The data processing system of claim 1, wherein the digital healthcare service recommendations include a prediction of the savings that may be achieved by utilizing digital health services recommended in the digital healthcare service recommendations.

8. A method implemented in a data processing system for machine-learning driven data analysis and reminders, the method comprising:

obtaining digital healthcare service provider information associated with one or more digital healthcare service providers to provide digital healthcare point solutions to employees of an employer;

converting the digital healthcare service provider information from a first format to a second format to generate standardized digital healthcare service provider information, the second format being associated with a standard schema;

receiving, from a client device associated with a user, query parameters information identifying characteristics of digital healthcare service providers for providing digital care health services;

converting the query parameters information from a third format to a fourth format to generate standardized query parameter information, the fourth format being associated with the standard schema;

providing the standardized query parameter information as an input to a first machine learning model;

analyzing the standardized query parameter information to obtain category information, the first machine learning model being trained using first training data formatted according to the standard schema to recognize a category or categories of services associated with the standardized query parameter information;

providing the category information and the digital healthcare service provider information as an input to a second machine learning model;

analyzing the category information and the digital healthcare service provider information using the second machine learning model to obtain digital healthcare service recommendations, the second machine learning model being trained using second training data formatted according to the standard schema to predict digital health services that the employer may provide to the employees of the employer based on the category information and categories of digital health services included in the digital healthcare service provider information; and providing, via a network connection, the digital healthcare service recommendations to the client device associated with the user.

9. The method of claim 8, wherein the machine-readable medium includes instructions configured to cause the processor to perform operations of:

obtaining an electronic copy of demographic information associated with the employees of the employer; and converting the demographic information from a third format to a fourth format to generate standardized demographic information, the fourth format being associated with the standard schema.

10. The method of claim 9, further comprising:

providing the standardized demographic information as an input to a third machine learning model;

analyzing the standardized demographic information using the third machine learning model to obtain additional category information, the third machine learning model being trained using third training data formatted according to the standard schema to predict categories of healthcare services that may be relevant to the employees of the employer based on the standardized demographic information; and providing the category information, the additional claim category information, and the digital healthcare service provider information as an input to a second machine learning model.

11. The method of claim 8, further comprising:

causing to be displayed on the computing device associated with the user an employer dashboard user interface that includes a representation of the digital healthcare service recommendations.

12. The method of claim 11, wherein the representation of the digital healthcare service recommendations includes controls, which when activated, establish a connection with a server of a respective digital health service provider to obtain services for the employees of the user.

13. The method of claim 11, further comprising:

causing the user device to display a user interface that guides the user through a process of setting up a contract with the respective digital health service provider.

14. The method of claim 8, wherein the digital healthcare service recommendations include a prediction of the savings that may be achieved by utilizing digital health services recommended in the digital healthcare service recommendations.

15. A machine-readable medium on which are stored instructions that, when executed, cause a processor of a programmable device to perform operations of:

obtaining digital healthcare service provider information associated with one or more digital healthcare service providers to provide digital healthcare point solutions to employees of an employer;

converting the digital healthcare service provider information from a first format to a second format to generate standardized digital healthcare service provider information, the second format being associated with a standard schema;

receiving, from a client device associated with a user, query parameters information identifying characteristics of digital healthcare service providers for providing digital care health services;

converting the query parameters information from a third format to a fourth format to generate standardized query parameter information, the fourth format being associated with the standard schema;

providing the standardized query parameter information as an input to a first machine learning model;

analyzing the standardized query parameter information to obtain category information, the first machine learning model being trained using first training data formatted according to the standard schema to recognize a category or categories of services associated with the standardized query parameter information;

providing the category information and the digital healthcare service provider information as an input to a second machine learning model;

analyzing the category information and the digital healthcare service provider information using the second machine learning model to obtain digital healthcare service recommendations, the second machine learning model being trained using second training data formatted according to the standard schema to predict digital health services that the employer may provide to the employees of the employer based on the category information and categories of digital health services included in the digital healthcare service provider information; and providing, via a network connection, the digital healthcare service recommendations to the client device associated with the user.

16. The machine-readable medium of claim 15, further comprising instructions configured to cause the processor to perform operations of:

obtaining an electronic copy of demographic information associated with the employees of the employer; and converting the demographic information from a third format to a fourth format to generate standardized demographic information, the fourth format being associated with the standard schema.

17. The machine-readable medium of claim 16, further comprising instructions configured to cause the processor to perform operations of:

providing the standardized demographic information as an input to a third machine learning model;

analyzing the standardized demographic information using the third machine learning model to obtain additional category information, the third machine learning model being trained using third training data formatted according to the standard schema to predict categories of healthcare services that may be relevant to the employees of the employer based on the standardized demographic information; and providing the category information, the additional claim category information, and the digital healthcare service provider information as an input to a second machine learning model.

18. The machine-readable medium of claim 15, further comprising instructions configured to cause the processor to perform an operation of:

causing to be displayed on the computing device associated with the user an employer dashboard user interface that includes a representation of the digital healthcare service recommendations.

19. The machine-readable medium of claim 18, wherein the representation of the digital healthcare service recommendations includes controls, which when activated, establish a connection with a server of a respective digital health service provider to obtain services for the employees of the user.

20. The machine-readable medium of claim 18, further comprising instructions configured to cause the processor to perform an operation of:

causing the user device to display a user interface that guides the user through a process of setting up a contract with the respective digital health service provider.

* * * * *